(12) United States Patent
Vos

(10) Patent No.: US 8,008,433 B2
(45) Date of Patent: Aug. 30, 2011

(54) METHODS FOR PREVENTING OR TREATING BONE DISORDERS

(75) Inventor: Evert Vos, Albuquerque, NM (US)

(73) Assignee: Metabolic Pharmaceutical Limited, Melborne (AU)

( * ) Notice: Subject to any disclaimer, the term of this patent is extended or adjusted under 35 U.S.C. 154(b) by 581 days.

(21) Appl. No.: 11/579,124

(22) PCT Filed: May 4, 2005

(86) PCT No.: PCT/AU2005/000638
§ 371 (c)(1),
(2), (4) Date: Sep. 4, 2007

(87) PCT Pub. No.: WO2005/105132
PCT Pub. Date: Nov. 10, 2005

(65) Prior Publication Data
US 2008/0131521 A1   Jun. 5, 2008

(30) Foreign Application Priority Data
May 4, 2004   (AU) ................................ 2004902388

(51) Int. Cl.
*C07K 11/00*   (2006.01)
*C07K 14/61*   (2006.01)
(52) U.S. Cl. .................... 530/326; 530/324; 530/325
(58) Field of Classification Search ...... 514/2; 530/326, 530/325, 324
See application file for complete search history.

(56) References Cited

FOREIGN PATENT DOCUMENTS
WO    WO 01/04119 A1    1/2001
WO    WO 2004/033645 A2    4/2004

OTHER PUBLICATIONS

Degerblad M. (Acta Endocrinol 126, 387-93, 1992).*
O'Halloran D.J. (J. Clin. Endocrinol. Metab. 76, 1344-48, 1993).*
Johansson A. G (Journal of Clinical Endocrinology and Metabolism 81(1), 44-48, 1996).*
Kamikovski et. al.: "Does the Growth Hormone-Derived Peptide AOD9604 Have an Anabolic Effect on bone?", abstract, Bone 44 (2009) S211-S231 (1 pg).
English Translation of Notification of Reasons for Refusal in Japanese Patent Application No. 2007-511768 dated Mar. 15, 2011.
O. Ortoft et al., "Qualitative Alterations of Cortical Bone in Female Rats After Long-Term Administration of Growth Hormone and Glucocorticoid", Bone, vol. 18, No. 6, Jun. 1995, pp. 581-590.
Claes Ohlsson et al., "Growth Hormone and Bone", Endocrine Review, 19(1), pp. 55-79, 1998.
Andrea Giustina et al., "Effects of Recombinant Human Growth Hormone (GH) on Bone and Intermediary Metabolism in Patients Receiving Chronic Glucocorticoid Treatment with Supressed Endogenous GH Response to GH-Releasing Hormone", Journal of Clinical Endocrinology and Metabolism, vol. 80, No. 1, pp. 122-129, 1996.

* cited by examiner

*Primary Examiner* — David Lukton
(74) *Attorney, Agent, or Firm* — Stephen A. Bent; Foley & Lardner LLP

(57) ABSTRACT

The present invention relates to a method of preventing or treating a bone disorder in a mammal, comprising administering to the mammal a therapeutically effective amount of a peptide having ability to modulate lipid metabolism but having no appreciable effect on IGF-1.

13 Claims, 11 Drawing Sheets

FIGURE 2  Experiment Summary and Timeline a)
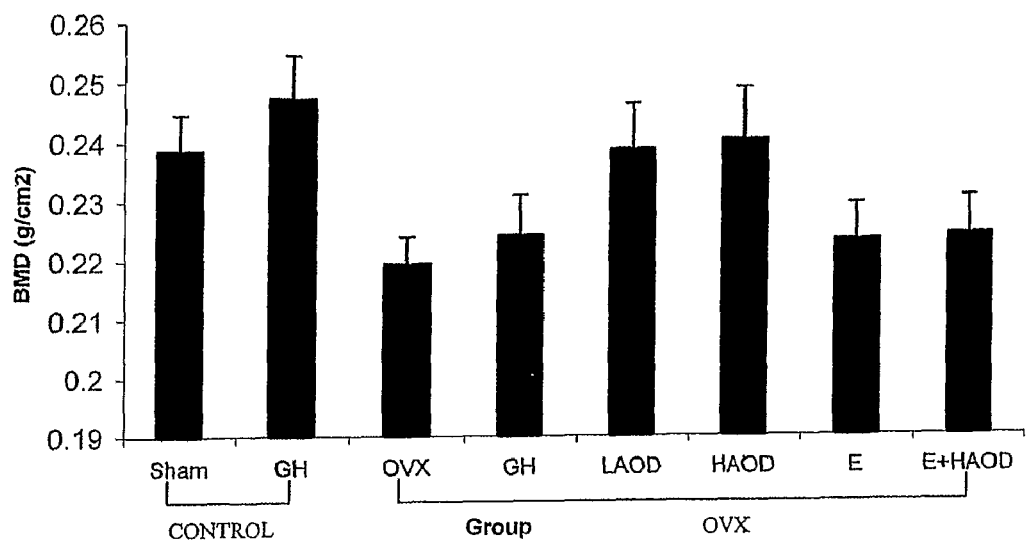
b)
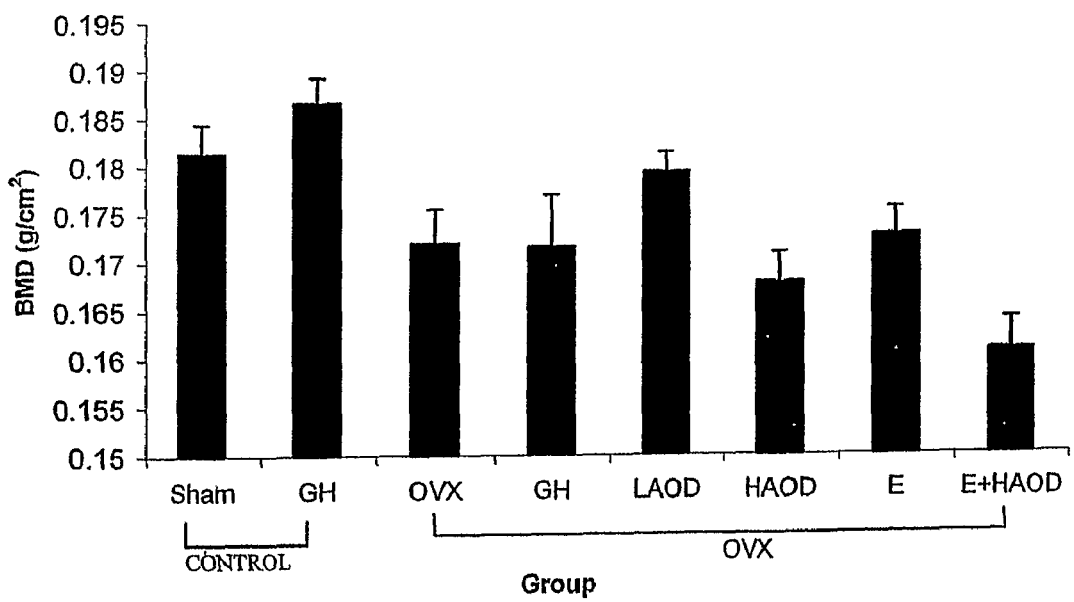
FIGURE 3 a)
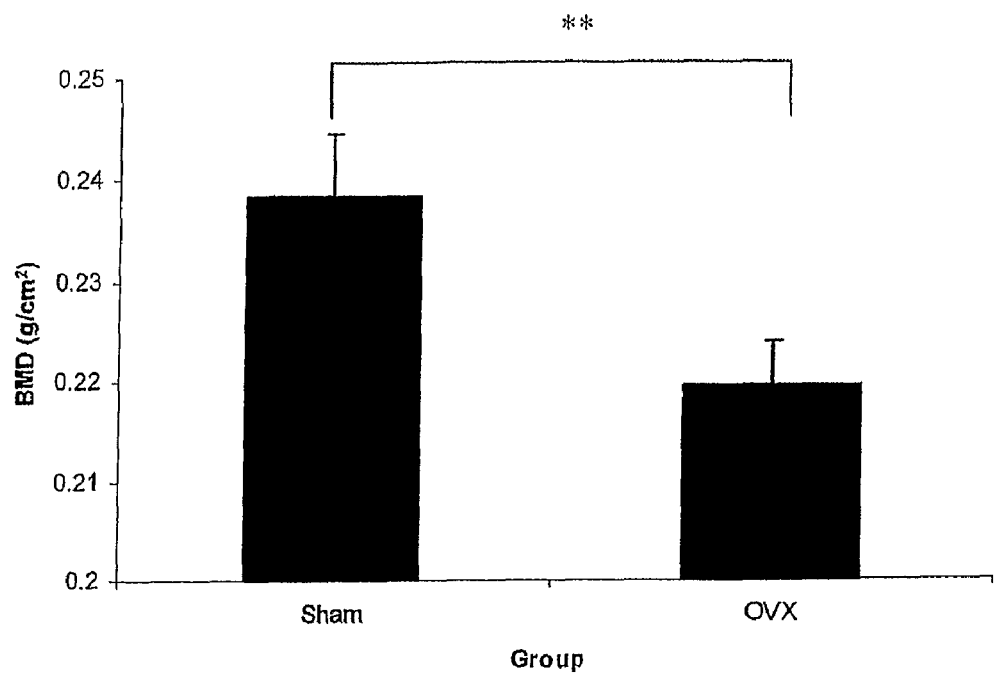
b)
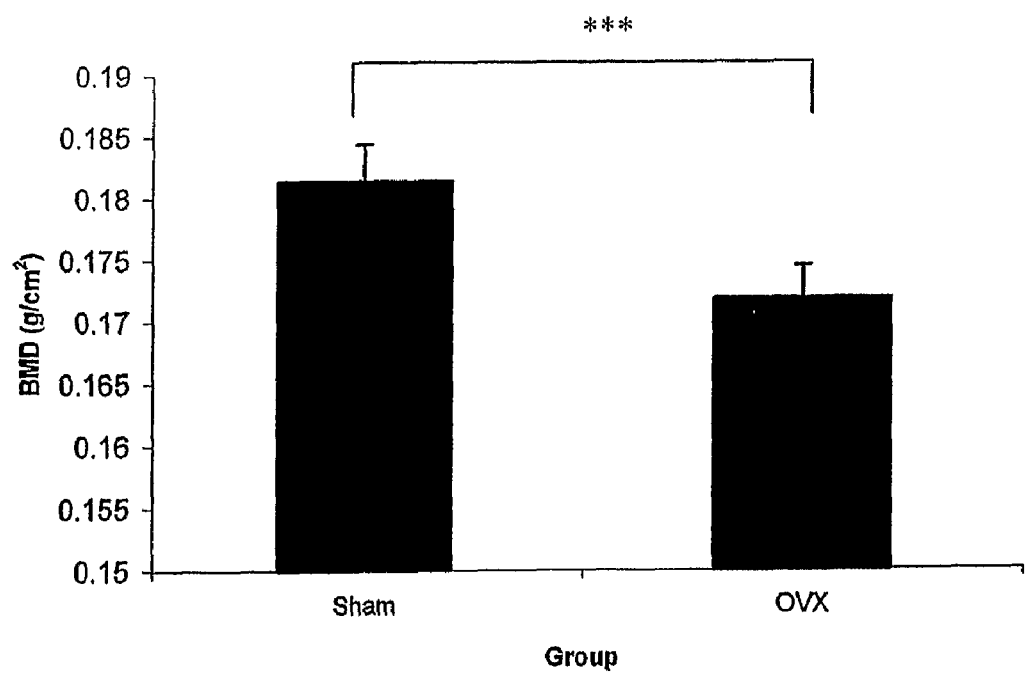
FIGURE 4

METHODS FOR PREVENTING OR TREATING BONE DISORDERS

RELATED APPLICATIONS

This application is a national stage application under 35 U.S.C. §371 of PCT/AU2005/000638, filed 4 May 2005, which claims priority to Australian application no. 2004902388, filed 4 May 2004, each of which is hereby incorporated by reference in its entirety.

This invention relates to methods for the prevention or treatment of bone disorders and compounds for use in such methods. In particular, the invention relates to methods for preventing or treating bone disorders characterized by altered bone metabolism, including osteoporosis, including post-menopausal osteoporosis, osteopenia, Paget's disease, osteolytic metastasis in cancer patients, osteodistrophy in liver disease and the altered bone metabolism caused by renal failure or haemodialysis, bone fracture, bone surgery, aging, pregnancy, and malnutrition.

BACKGROUND OF THE INVENTION

All references, including any patents or patent application, cited in this specification are hereby incorporated by reference to enable full understanding of the invention. Nevertheless, such references are not to be read as constituting an admission that any of these documents forms part of the common general knowledge in the art, in Australia or in any other country. The discussion of the references states what their authors assert, and the applicants reserve the right to challenge the accuracy and pertinency of the cited documents.

Bone is a living tissue that is constantly being renewed. It contains cells and specialized collagen fibres, encrusted with a crystalline mineral. Together, the minerals, cells, and fibres form an organic matrix or "osteoid".

Bone is constantly undergoing bone formation by osteoblasts and bone resorption by osteoclasts. If blood calcium levels are lowered, resorption of the bone increases to fulfil calcium requirements elsewhere in the body.

Altered bone metabolism can be characterized by a misbalance between bone formation and bone resorption. It can occur in relation to several types of disorders. Examples are osteoporosis, osteopenia, Paget's disease, osteolytic metastasis in cancer patients, osteodistrophy in liver disease and the altered bone metabolism caused by renal failure or haemodialysis, bone fracture, bone surgery, aging, pregnancy, and malnutrition.

Bone loss is accelerated with aging. The major bone disease in the older population is osteoporosis. This disease is characterized by extensive bone loss leading to an increase in bone fragility and a greater risk of fractures. It causes considerable pain, disability, disfigurement and loss of independence, and is a cost and burden to health services. Internationally, more than 1.5 million fractures occur every year as a result of osteoporosis.

There are two types of osteoporosis recognized. The first typically occurs between the ages of 50 and 75 and affects six times as many women (post-menopausal osteoporosis) as men. The second type is referred to as senile osteoporosis and affects both men and women over 75 years of age and does not involve greater than normal bone loss. The risk factors for both types of osteoporosis are high caffeine intake, alcohol consumption, low body weight and low calcium intake.

The most prominent and well-documented cause of post-menopausal osteoporosis is estrogen deficiency. After the menopause, the ovaries cease to produce this hormone, which directly relates to loss of bone mineral content. A known treatment for post-menopausal symptoms, including osteoporosis, is hormone replacement therapy (HRT), and this estrogen replacement effectively prevents the development of osteoporosis. However the use of HRT may have serious side effects, e.g. breast tissue growth stimulation, and an alternative treatment for post-menopausal osteoporosis is required.

The main causes of other types of bone disorders have yet to be determined and a treatment for such disorders is required.

It is an aim of a preferred embodiment of the present invention to provide a method for the prevention or treatment of bone disorders and compositions for use in such methods.

SUMMARY

According to the present invention in a first aspect, there is provided a method of preventing or treating bone disorders in a mammal, comprising administering to the mammal a therapeutically effective amount of a peptide having ability to modulate lipid metabolism without having an appreciable effect on insulin-like growth factor-1 (IGF-1).

In Australian patent No. 693478 by Monash University, we described the use of a peptide derived from the carboxyl-terminal sequence of human growth hormone, or corresponding regions from growth hormone of other mammalian species, for the control of obesity. This region of growth hormone has the ability to modulate lipid metabolism. In particular, a synthetic peptide corresponding to amino acid residues 177-191 of the human growth hormone sequence (hereinafter referred to as hGH 177-191) was found to reduce body weight gain and adipose tissue mass in a model system for obesity, the C57B1/6J (Ob/Ob) mouse. A subsequent application, PCT/AU98/00724 by Metabolic Pharmaceuticals Ltd, discloses analogues of the hGH177-191 peptide which share this activity. The entire disclosures of AU693478 and PCT/AU98/00724 are incorporated herein by this reference.

Our application, PCT/AU00/01362 (WO01/33977), discloses the surprising oral activity of such peptides.

Studies of AOD9604 (Tyr-hgH 177-191) have now been performed on the skeleton in an aged rat model for post-menopausal osteoporosis. As peptides corresponding to C-terminal fragments of human growth hormone described in our earlier applications have none of the normal growth effects of normal full length growth hormone and have no effect on IGF-1 (which mediates the growth effects of human growth hormone), it was expected that no effect on bone metabolism would be found. Surprisingly, we have found, in two studies, that AOD9604 has effects on bone growth, and indeed the effect on preventing bone loss was found to be better than estrogen.

The inventor has therefore recognized that a peptide corresponding to a C-terminal fragment of human growth hormone (AOD9604) has an effect on bone metabolism. The inventor therefore proposes that all of the C-terminal fragments of human growth hormone that they have previously shown to have ability to modulate lipid metabolism will have an effect similar to AOD9604 on bone metabolism. Accordingly the inventors propose that all of the peptides that they have previously shown to have ability to modulate lipid metabolism without affecting IGF-1 can be used to treat or prevent bone disorders.

According to a second aspect, the invention provides the use of a peptide having ability to modulate lipid metabolism without having an appreciable effect on IGF-1 in the manufacture of a medicament for use in treating or preventing bone disorders.

In a third aspect, the present invention provides a pharmaceutical formulation for use in preventing or treating bone disorders, which formulation comprises a peptide having ability to modulate lipid metabolism without having an appreciable effect on IGF-1 and a pharmaceutically acceptable carrier.

The formulation according to the third aspect may further comprise one or more agents for treating or preventing bone disorders.

The bone disorders that may be treated by the method of the first aspect or the medicament of the second aspect include those disorders that are characterized by altered bone metabolism.

The bone disorder may be, amongst others, osteoporosis, including post-menopausal osteoporosis, osteopenia, Paget's disease, osteolytic metastasis in cancer patients, osteodistrophy in liver disease and the altered bone metabolism caused by renal failure or haemodialysis, bone fracture, bone surgery, aging, pregnancy, and malnutrition.

The invention may be particularly suitable for the treatment or prevention of post-menopausal osteoporosis.

BRIEF DESCRIPTION OF THE FIGURES

FIG. 3: Bone Mineral Density (BMD) of all treatment groups after 12 weeks of Treatment according to Example 2a) Lumbar Vertebrae (L4+L5) b) Femur.

FIG. 4: Bone Mineral Density of a) lumbar vertebrae (L4+L5) and b) femur, examining ovariectomy model. significance assigned at $p<0.05$, *trend assigned at $p<0.1$).

DETAILED DESCRIPTION

Figure 1:
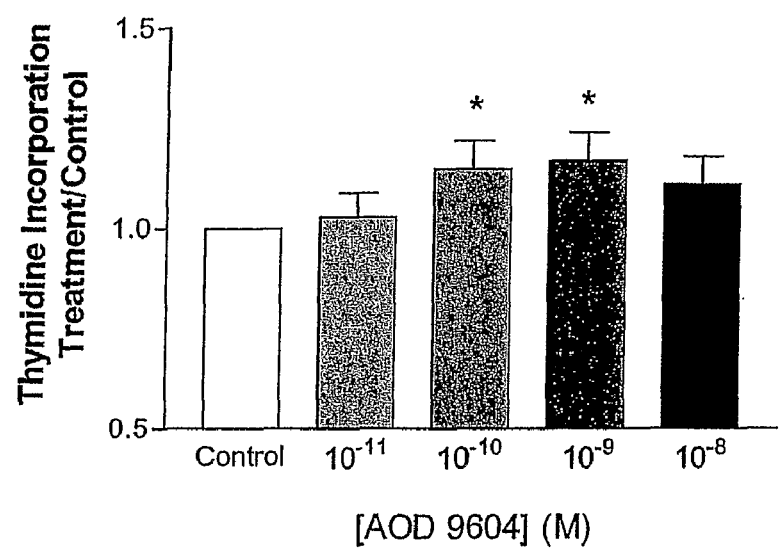
FIG. 1: Bar graph of concentration of AOD9604 against the amount of thymidine incorporation in primary osteoblast cultures in an osteoblast proliferation assay.

A peptide having ability to modulate lipid metabolism without having an appreciable effect on IGF-1 especially corresponds to the C-terminal amino acid sequence of growth hormone. Such a peptide is termed a "C-terminal growth hormone fragment." For the purposes of this specification, the term "C-terminal growth hormone fragment" is to be understood to mean a peptide fragment from the carboxy-terminal region of the amino acid sequence of a mammalian growth hormone which is able to reduce lipogenic activity; and, or to stimulate lipolysis.

"Peptide" as used herein means any chain of amino acids from 2 to 50 amino acid residues in length, preferably 2 to 20, more preferably about 15 amino acid residues in length. Accordingly the term peptide as used herein also encompasses polypeptides and may be used interchangeably therewith. The only proviso is that any peptide for use in accordance with the present invention does not have the full length sequence of human growth hormone or an analogue thereof from another species. Full length growth hormone is capable of modulating lipid metabolism but also modulates IGF-1. Accordingly full length growth hormone does not fall within the scope of the peptides for use in accordance with the present invention.

Preferably the peptide used in accordance with the present invention has the ability to stimulate the activity of hormone-sensitive lipase, a key enzyme in lipolysis, and to inhibit acetyl CoA carboxylase, a key enzyme in lipogenesis.

Preferably the peptide used in accordance with the present invention comprises at least the disulphide-bonded loop of a mammalian growth hormone.

The term "growth hormone fragment" also encompasses peptides which are functional analogues of the native carboxy-terminal sequences of mammalian growth hormones, in that the analogue peptide is capable of modulating lipid metabolism without an appreciable effect on IGF-1. Such analogues may be derived from natural sources, produced by recombinant DNA technology, or synthesised using conventional peptide synthetic methods. Such peptides synthetic methods are to be understood to include combinatorial methods. Preferably such analogues include a disulphide bond which confers a cyclic configuration on the peptide. In particular, all of the active peptides disclosed in AU 693478 and PCT/AU98/00724 are to be understood to be within the scope of this invention, for example:

| Ref No. | STRUCTURE |
|---|---|
| 9502 | Leu Arg Ile Val Gln Pen Arg Ser Val Glu Gly Ser Pen Gly Phe<br>SEQ ID NO:1 |
| 9405 | CH3CO-Leu Arg Ile Val Gln Cys Arg Ser Val Glu Gly Ser Cys Gly Phe<br>SEQ ID NO:2 |
| 9410 | H-Leu Arg Ile Val Gln Cys Arg Ser Val Glu Gly Ser Cys Gly Phe<br>SEQ ID NO:3 |
| 9404 | Leu Arg Ile Val Gln Cys Arg Ser Val Glu Gly Ser Cys Gly Phe-CONH$_2$<br>SEQ ID NO:4 |
| 9407 | Leu Arg Ile Val Gln Cys Lys Ser Val Gln Gly Ser Cys Gly Phe<br>SEQ ID NO:5 |

-continued

| Ref No. | STRUCTURE |
|---|---|
| 9408 | Leu Arg Ile Val Gln Cys <u>Lys Ser Val Glu</u> Gly<br>(amide bond)<br>Ser Cys Gly Phe<br>SEQ ID NO:6 |
| 9604 | Tyr Leu Arg Ile Val Gln Cys Arg Ser Val Glu<br>Gly Ser Cys Gly Phe<br>SEQ ID NO:7 |
| 9605 | Lys Leu Arg Ile Val Gln Cys Arg Ser Val Glu<br>Gly Ser Cys Gly Phe<br>SEQ ID NO:8 |
| 9618 | Lys Lys Leu Arg Ile Val Gln Cys Arg Ser Val<br>Glu Gly Ser Cys Gly Phe<br>SEQ ID NO:9 |
| 9607 | Ala Arg Ile Val Gln Cys Arg Ser Val Glu Gly<br>Ser Cys Gly Phe<br>SEQ ID NO:10 |
| 9606 | Leu Lys Ile Val Gln Cys Arg Ser Val Glu Gly<br>Ser Cys Gly Phe<br>SEQ ID NO:11 |
| 9608 | Leu Arg Ala Val Gln Cys Arg Ser Val Glu Gly<br>Ser Cys Gly Phe<br>SEQ ID NO:12 |
| 9403 | Leu Arg Lys Val Gln Cys Arg Ser Val Glu Gly<br>Ser Cys Gly Phe<br>SEQ ID NO:13 |
| 9609 | Leu Arg Ile Ala Gln Cys Arg Ser Val Glu Gly<br>Ser Cys Gly Phe<br>SEQ ID NO:14 |
| 9610 | Leu Arg Ile Val Ala Cys Arg Ser Val Glu Gly<br>Ser Cys Gly Phe<br>SEQ ID NO:15 |
| 9612 | Leu Arg Ile Val Gln Cys Arg Ala Val Glu Gly<br>Ser Cys Gly Phe<br>SEQ ID NO:16 |
| 9613 | Leu Arg Ile Val Gln Cys Arg Ser Ala Glu Gly<br>Ser Cys Gly Phe<br>SEQ ID NO:17 |
| 9615 | Leu Arg Ile Val Gln Cys Arg Ser Val Glu Ala<br>Ser Cys Gly Phe<br>SEQ ID NO:18 |
| 9616 | Leu Arg Ile Val Gln Cys Arg Ser Val Glu Gly<br>Ala Cys Gly Phe<br>SEQ ID NO:19 |
| 9602 | Leu Arg Ile Val Gln Cys Arg Ser Val Glu Gly<br>Ser Cys Ala Phe<br>SEQ ID NO:20 |
| 9501 | Leu Arg Ile Val Gln Cys Arg Ser Val Glu<br>D-Ala Ser Cys D-Ala Phe<br>SEQ ID NO:21 |
| 9601 | Leu Arg Ile Val Gln Cys Arg Ser Val Glu Gly<br>Ser Cys Gly Ala<br>SEQ ID NO:22 | wherein the amino acid residue abbreviations used are in accordance with the standard peptide nomenclature:
Gly=Glycine; Ile=Isoleucine;
Glu=Glutamic Acid; Phe=Phenylalanine;
Cys=Cysteine; Arg=Arginine; Gln=Glutamine;
Leu=Leucine; Ser=Serine; Val=Valine;
Lys=Lysine; Ala=Alanine;
Asp=Aspartic acid; His=Histidine;
Orn=Ornithine; Tyr=Tyrosine;
Pen=Penicillamine(p, p'-Dimethyl-Cysteine).

All amino acids, except for glycine, are of the L-absolute configuration, unless indicated as D-absolute configuration. All the above peptides above have a cyclic disulfide bond between Cys(182) and Cys(189) or Pen(182) and Pen(189) as appropriate.

Preferably the peptide comprises amino acids 182-189 (hGH 182-189), more preferably amino acids 177-191 of human growth hormone (hGH 177-191). Even more preferably the peptide is the human growth hormone analogue AOD9604 (Tyr-hGH 177-191). However, it will be clearly understood that the invention is also applicable to peptides corresponding to the amino acid sequences of growth hormones of other mammalian species, including but not limited to those of domestic mammals such as cattle, sheep, pigs and horses, companion animals such as cats and dogs, and zoo animals including felids, canids, and non-human primates. There is strong conservation of the sequence of this region of growth hormone across species, as set out in PCT/AU98/00724 and references cited therein.

The peptide may also be conjugated to a fusion partner to enable easier biosynthesis and/or delivery. It may be incorporated in a conventional pharmaceutical composition, or may be present in a genetically-modified food, such as disclosed in WO 01/33997.

The peptide may be administered in a pharmaceutical composition together with a pharmaceutically acceptable carrier for administration.

The peptide may be administered by any suitable route, and the person skilled in the art will readily be able to determine the most suitable route and dose for the condition to be treated. The peptide may be administered orally, sublingually, buccally, intranasally, by inhalation, transdermally, topically, or parenterally in dosage unit formulations containing conventional non-toxic pharmaceutically acceptable carriers, adjuvants, and vehicles. The term parenteral as used herein includes subcutaneous, intravenous, intramuscular, intrathecal, intracranial, injection or infusion techniques.

Dosage will be at the discretion of the attendant physician or veterinarian, and will depend on the nature and state of the condition to be treated, the age and general state of health of the subject to be treated, the route of administration, and any previous treatment which may have been administered. The dosing interval may be once per week, once per day or continuous time release.

Preferably, the mammal is suffering from a bone disorder characterized by altered bone metabolism, such as osteoporosis, including post-menopausal osteoporosis, osteopenia, Paget's disease, osteolytic metastasis in cancer patients, osteodistrophy in liver disease and the altered bone metabolism caused by renal failure or haemodialysis, bone fracture, bone surgery, aging, pregnancy, and malnutrition. The mammal may also be growth hormone-deficient.

The mammal may be a human, or may be a domestic or companion animal. While it is particularly contemplated that the present invention is used in medical treatment of humans, it is also applicable to veterinary treatment, including treatment of companion animals such as dogs and cats, and domestic animals such as horses, cattle and sheep, or zoo animals such as non-human primates, felids, canids, bovids, and ungulates.

Preferably the mammal is a human. The human may be a child or an adult.

Methods and pharmaceutical carriers for preparation of pharmaceutical compositions are well known in the art, as set out in textbooks such as Remington's Pharmaceutical Sciences, 20th Edition, Williams and Williams, Pennsylvania, USA (2000).

As used herein, a "pharmaceutically acceptable carrier" is a pharmaceutically acceptable solvent, suspending agent, excipient or vehicle for delivering the growth hormone fragment and/or pharmaceutically-active agent to the subject. The carrier or diluent, and other excipients, will depend on the route of administration, and again the person skilled in the art will readily be able to determine the most suitable formulation for each particular case.

Analogues of the peptides described herein are included within the scope of the invention, provided that they are functionally active. As used herein, the terms "functionally active" and "functional activity" in reference to an analogue means that analogue is capable of (or has ability for) modulating lipid metabolism without having an appreciable effect on IGF-1.

The ability of peptides or analogues used in accordance with the present invention to prevent or treat bone disorders may be evidenced by osteoblast formation activity as described in the examples.

Analogues as used herein includes amino acid sequence variants of the peptide amino acid sequences provided. Sequence variants include deletions, insertions or substitutions of amino acid residues within the growth hormone fragment amino acid sequence set out above. Any combination of deletion, insertion, and substitution may be made to arrive at an amino acid sequence variant of the growth hormone fragment, provided that the variant possesses the desired functional characteristics described herein; i.e ability to modulate lipid metabolism without having an appreciable effect on IGF-1.

Particularly, a test to determine whether a variant is functionally active is whether the variant stimulates thymidine incorporation in primary fetal rat osteoblasts to a statistically significant level (see Example 1 for further details).

If such substitutions do not result in a change in functional activity, then more substantial changes, denoted exemplary substitutions in Table 1, or as further described below in reference to amino acid classes, may be introduced, and the resulting variant growth hormone fragment analyzed for functional activity.

A person skilled in the art would be able to determine whether a peptide has the ability to modulate lipid metabolisms but has no appreciable effect on IGF-1 by methods of the common general knowledge.

As used herein the term "no appreciable effect" means that the effect on IGF-1 is not statistically significant and that if any effect of a peptide is registered in an assay it can be considered negligible.

One way in which a skilled person may determine if a peptide is capable of modulating lipid metabolism is by performing a lipolysis assay as described in Example A. In brief rats are treated and sacrificed, adipose tissue is obtained from treated and control rats and placed in vials and terbutaline added. The vials are incubated at 37° C. for 1 hour, gassed with carbon and assayed in a standard glycerol assay, for example using an assay kit such as Sigma GPO-337.

The lipogenesis assay described in Example B is another method by which a person skilled in the art may determine if a peptide is able to modulate lipid metabolism.

To determine is a peptide has an appreciable effect on IGF-1 a person skilled in the art may perform an IGF-1 assay on a blood sample (for example from a mouse). A suitable assay kit is available from R & D Systems, Inc., with catalogue number DY791. This is a sandwich ELISA using hamster anti-mouse IGF-1 as capture antibody and goat anti-mouse IGF-1 as detection antibody. Full details of the test are provided as Example C.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

As used herein, the terms "therapeutically effective amount" and "therapeutic amount" are synonymous, and mean an amount of a peptide of the present invention effective to yield a desired therapeutic response.

The specific therapeutically effective amount will obviously vary with such factors as the particular condition being treated, the type of mammal being treated, the physical condition and clinical history of the mammal, the duration of the treatment, the nature of concurrent therapy (if any), and the specific formulations employed and the structure of the peptide.

Generally, the terms "treating", "treatment" and the like are used herein to mean affecting a subject, tissue or cell to obtain a desired pharmacological and/or physiological effect. The effect may be prophylactic in terms of completely or partially preventing bone loss, and/or may be therapeutic in terms of increasing bone formation and/or osteoblast deposition.

"Treating" as used herein covers any method of treatment of, or prevention of disease in a mammal, particularly a human, and includes preventing the disease from occurring in a subject who may be predisposed to the disease, but has not yet been diagnosed as having it; inhibiting the disease, i.e., arresting its development; or relieving or ameliorating the effects of the disease, i.e., cause regression of the effects of the disease.

The third aspect of the invention includes various pharmaceutical compositions useful for ameliorating bone disorders. The pharmaceutical compositions according to one embodiment of the invention are prepared by bringing a peptide corresponding to a C-terminal growth hormone fragment, analogue, variant or salts thereof and one or more agents active against bone disorders together into a form suitable for administration to a subject using carriers, excipients and additives or auxiliaries.

The additional agents active against bone disorders include calcium, bone minerals, such as magnesium and boron, gamma linolenic acid, vitamins such as vitamin D and vitamin K, estrogens or one or more estrogen mimicking compounds used in Estrogen Replacement Therapy, biphosphonates and, isoflavones.

Calcium may be added to increase calcium deposition in bones. The calcium source can be any suitable inorganic or organic compound containing calcium. Examples are inorganic calcium salts, for example calcium chloride, calcium phosphate, calcium sulphate, calcium oxide, calcium hydroxide or calcium carbonate. Examples of organic calcium compounds are milk powder or calcium caseinate, calcium citrate, calcium malate, calcium citrate malate or calcium lactate. The amount of calcium is preferably 200 to 1500 mg per daily dose.

Bone minerals may be added to increase bone strength. Preferably the preparation contains 100 mg to 500 mg magnesium and 2 mg to 6 mg boron per daily dose.

Gamma linolenic acid may be used to regulate calcium metabolism, preferably in an amount of 25 mg to 100 mg per daily dose.

Vitamins may be added as cofactors for optimal bone metabolism. Preferably, daily vitamin K dose should be 25 pg to 5 mg vitamin K. Vitamin D is used to increase calcium uptake from the gut. Preferably 200 IU to 800 IU per daily dose is present in the preparation.

Estrogens or one or more estrogen mimicking compounds used in Estrogen Replacement may also be included in the formulation. Examples of estrogen-mimicking compounds are phytoestrogens, like genistein, lignans or coumerans or pharmaceutical preparations like17p-estradiol, esterified estrogens, estrone sulfate, conjugated equine estrogen, and ethinylestradiol. For the phytoestrogens the amount of these compounds is 5-100 mg per daily dose. For the pharmaceutical preparations the active amount is defined by the instructions of the manufactures.

One or more biphosphonates may be used to inhibit the osteoclastic bone resorption. Examples of these compounds are alendronate and risedronate. Preferably the amount of these compounds is 5 mg to 50 mg per daily dose.

Isoflavones may be obtained (isolated) from soy or black cohosh or can be synthetic isoflavones. Isoflavones can be added in an amount of 10 to 75 mg per daily dose.

The formulations according to the third aspect of the invention can further contain other sources of energy, such as fats and carbohydrates, proteins, vitamins, minerals, fibers, flavors, preservatives, colorants, sweeteners, etc.

Any chemically compatible combination of pharmaceutically-active agents is within the scope of the invention, provided that the combination does not eliminate the activity of the growth hormone fragment of this invention.

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects.

An effective amount of the growth hormone fragment to be employed therapeutically will depend, for example, upon the therapeutic objectives, the route of administration, and the condition of the subject. Accordingly, it will be necessary for the therapist to titrate the dosage and modify the route of administration as required to obtain the optimal therapeutic effect. A typical daily dosage might range from about 1 µg/kg to up to 100 mg/kg or more, depending on the mode of delivery.

Dosage levels of the growth hormone fragment will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

For the purposes of this specification it will be clearly understood that the word "comprising" means "including but not necessarily limited to", and that the word "comprises" has a corresponding meaning.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention will now be described by way of reference only to the following non-limiting examples.

EXAMPLES

Rat Treatment Protocol

Rats: 16 Male Wistar rats.

Feed lean Wistar rats on a high fat diet for 29 days. Weigh rats weekly (including day 0 of drug administration). Keep rats on a high fat diet during drug or saline administration.

Treat 8 male Wistar (lean) rats (adult age) with drug (in saline) administered by an effective administration route. Treat 8 male Wistar (lean) rats (adult age) with saline (equivalent volume) daily also for 29 days.

Measure body weight on days 0, then weekly. Animals must be administered daily at the same time (8:30-9:30 am).

On day 28, take blood sample from all rats and store appropriately.

On day 29 following administration, do not starve animals before sacrifice and allow free access to food and water.

Leave rats for 2 hours after last administration (with free access to food and water). During this period, make buffers, drug stocks (terbutaline-HCl from Sigma) and prepare dissection equipment and working area.

To each vial (×6 for each dilution per rat) add 1.8 ml of KRB (see appendix 3) buffer (containing 2% BSA and 1 mM glucose), cover and leave until tissue dissection. Stock solutions of terbutaline will be 10× concentrated, and following tissue being added to the vial, 200 µl shall be added to every vial just prior to incubation. This shall give the final concentrations of terbutaline of 0 µmol/L) 0.1 µmol/L and 0.5 µmol/L. Cover and leave the terbutaline in the refrigerator till before incubation (light sensitive!!).

Kill rats 2 hours after last administration by immediate decapitation. Immediately remove the epididymal adipose tissue, and rinse thoroughly in saline (room temperature).

Example A

Lipolysis Test for Ability of a Peptide to Modulate Lipid Metabolism

Dissect one adipose pad into 18 even pieces (8 replicates per terbutaline treatment) and place each piece immediately into the 1.8 ml KRB buffer. Record the weights and minimise variation of the incubation time by cutting all pieces first, and then placing them into the vials.

Add 200 µl of the terbutaline solution to each vial containing tissue, and place immediately into the incubator.

Incubate for 60 minutes at 37° C. gassed with carbogen.

Following the incubation, remove 100 µl of the incubation solution and place into eppendorfs. Take 10 µl of this and use in the standard glycerol assay kit (Sigma GPO-337). Freeze remaining 90 µl mixture at −80° C.

Example B

Lipogenesis Test for Ability of a Peptide to Modulate Lipid Metabolism

Take the second adipose pad from each rat. Cut the tissue into pieces of similar weight (200 mg). Collect 6 pieces of tissue for each rat.

Place each piece of tissue into 10 ml conical flasks containing 2 ml KRB buffer/2% BSA, combine [$^{12}$C]-glucose with [$^{14}$C]-glucose (final specific activity 0.05 µCi/µmol) and human insulin (100 µU/ml). Incubate for 60 min in a 37° C. waterbath with constant shaking at 100 rpm and gassed with 95% $O_2$/5% $CO_2$.

Tissues are removed and rinsed 3 times on 0.9% NaCl, blotted and placed in glass screw-cap tubes (or falcon) containing 5 ml chloroform:methanol (2:1 v/v) solution and refrigerated at 4° C. overnight.

The tissue was removed (keep solution) and placed in a 10 ml centrifuge tube with 2 ml chloroform:methanol (2:1 v/v) solution, vortexed and refrigerated for 30 min. The extract solution from this step is pooled with the extract from step 4. The tissue is pressed with a glass rod to extract any remaining lipid.

The tissue is then mixed with 2 ml methanol:0.1% $MgCl_2$ solution (1:1 v/v) for 15 min at 4° C.

Pool extracts from step 5 and 6 and centrifuged at 10° C. at 6000×g for 10 min.

The upper layer is removed and discarded. 5 ml of the lower solution was transferred to a counting vial and left to evaporate under a stream of warm air overnight.

The dried material is resuspended in 1 ml chloroform to which 10 ml scintillant is added.

The radioactivity is measured for 60 sec and expressed as dpm/mg tissue.

Example C

Testing for Effect on IGF-1

The DuoSet ELISA development kit provided by R & D Research Systems, Inc. as catalogue number DY791 may be used to assay for effect on IGF-1. Each kit contains the basis components required for the development of sandwich ELISAs to measure IGF-1 in cell culture supernates and serum. The instructions for use of IGF-1 kit DY791 are reproduced at Annex 1.

Example 1

Materials
Peptide used: AOD 9604, 95% purity
Supplied by: Metabolic Pharmaceutical Ltd
Stored: −20° C.
Solubility: advised to dissolve at 1 mg/ml in saline; however, this produced a cloudy solution-centrifuged removed supernatant and assayed for protein.
Solution still contained >1 mg/ml, therefore assumed the precipitate was not protein.
Methods
Primary Osteoblast Proliferation Assay The AOD 9604 peptide was assayed in the primary fetal rat osteoblast culture system as detailed below.

Primary rat osteoblast cells are derived from sequential collagenase digestions of 21-day fetal rat calvariae. Digests 3-4 are pooled and grown in T-75 flasks in Dulbecco's modified Eagle medium (DMEM) containing 10% Fetal Bovine Serum (FBS). Cells are grown to confluence and then trypsinized and seeded into 24 well plates in minimum essential medium (MEM) containing 5% FBS and incubated 24 hours. Cells are then serum starved in MEM/0.1% BSA for 24 hours. Medium is replaced; growth substances added and cells incubated a further 24 hours. $^3$H-thymidine is added 4 hours prior to the end of this incubation period. Cells are washed and 10% TCA is added to wells and plates are left overnight at 4° C. Plates are then processed for thymidine incorporation.
Results
AOD has an Anabolic Affect on Primary Osteoblasts AOD significantly stimulated thymidine incorporation at concentrations of $10^{-10}$ M and $10^{-9}$ M in primary fetal rat osteoblasts (FIG. 1a). Significance was assessed using Student's t test.
Conclusions AOD was significantly mitogenic in primary osteoblast cultures. Therefore, it has the profile of a bone anabolic, and may have potential as a therapeutic compound in the bone area.

Example 2

This study looks at the effect of AOD 9604, on the skeleton in an aged rat model for post-menopausal osteoporosis. It was expected that AOD would not prevent the bone changes that occur as a result of ovariectomy in the rat.
Materials and Methods
(a) Animal Care and Housing This study included a total of 96 aged female Sprague-Dawley rats (*Rattus Norvegicus*), approximately nine months of age, obtained from Harlan (Harlan Farms, Indiana). The rats were randomly divided into 8 groups. For the duration of the 12 week study, they were housed at the animal facility of the Division of Comparative Medicine at the University of Toronto. The rats were kept in pairs in clear plastic cages with cornmeal bedding and a plastic tube for housing. Tap water and lab chow were available ad libitum to all rats. The room was monitored daily for constant temperature of 20.5° C. and humidity of 600.

(b) Drug Preparation and Administration

The rats in the GH and AOD treatment groups were injected five days per week for 12 weeks. All treatments were given by subcutaneous injection. The GH treatment group was treated with recombinant human GH (rhGH) (BresaGen, Adelaide, Australia). It was reconstituted following the manufacturer's instructions and was separated into daily aliquots and frozen at −70° C. for up to 4 week periods. The AOD treatment groups were treated with AOD 9406 (Formatech Inc., Andover Mass., U.S.A), which was stored lyophylized, at 4° C. The peptide was prepared according to the pharmaceutical company protocol. This was completed daily and used within 4 hours of preparation. The drug concentration was recalculated after 4, 8 and 10 weeks with the weight of the rats to ensure constant dosage throughout the experiment.

Experimental Design

Ninety-six aged Sprague-Dawley rats were randomly assigned to one of eight groups. The first two groups were sham operated. Group 1 was kept as a Sham control and Group 2 was treated with 2.5 mg/kg/day of recombinant human GH (rhGH) (BresaGen). The remaining six groups arrived from Harlan, ovariectomized (OVX). This surgery was performed approximately 8 days before the commencement of treatment. Group 3 was left as a control for the OVX model. Group 4 was given a treatment of 2.5 mg/kg/day of rhGH. Group 5 was treated with a low dose of AOD peptide (LAOD) 0.75 mg/kg/day and Group 6 was treated with a high dose of AOD peptide (HAOD) 2.0 mg/kg/day. The final two OVX groups received a slow release 17B-oestrogen pellet (0.01 mg/day, 17B-estradiol, Innovative Research of America, Sarasota Fla., U.S.A), which was implanted subcutaneously at the back of the neck. Group 7 was left as an estrogen control and Group 8 was given a high dose treatment of AOD peptide (HAOD) 2.0 mg/kg/day, Formatech Inc. A summary of the groups and treatments is given below.

| Group | Number of Rats | Model | Treatment | Dose (mg/kg) |
|---|---|---|---|---|
| 1 | 12 | Sham | — | — |
| 2 | 12 | Sham | RhGH | 2.5 |
| 3 | 12 | OVX | — | |
| 4 | 12 | OVX | RhGH | 2.5 |
| 5 | 12 | OVX | Low AOD | 0.75 |
| 6 | 12 | OVX | High AOD | 2.0 |
| 7 | 12 | OVX | Estrogen(E) | 0.01 mg/day |
| 8 | 12 | OVX | E + HAOD | 0.01 mg/day 2.0 |

Before the commencement of treatments, the rats were weighed and a 1 mL blood sample was taken. Blood samples were again taken after 4, 8 and 12 weeks. The blood samples were spun in serum separator tubes for 10 minutes at 100×g. The serum was drawn off and separated into four aliquots for further analysis. The aliquots were stored at −20° C. All rats were given a 30 mg/mL intraperitoneal injection of oxytetracycline (Tetraject LP, Bimeda—MTC Pharmaceuticals, Cambridge, ON, Canada) at 13 and 3 days before sacrifice. Any dilutions that were required were done using sterile saline.

Figure 2:
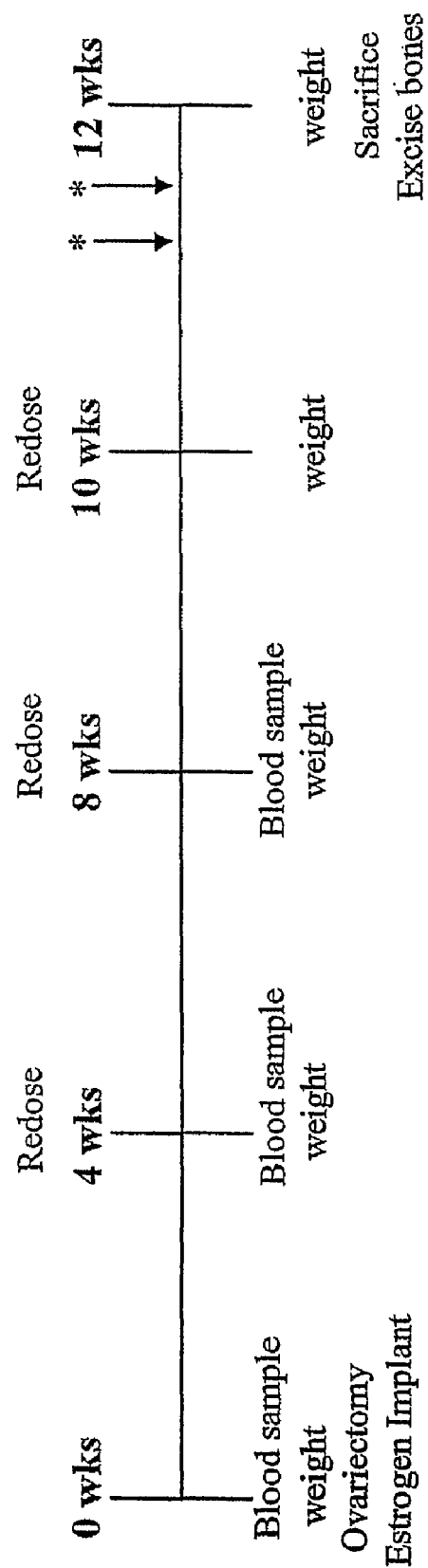
FIG. 2: Experimental design summary and timeline for Example 2.

At the end of the 12-week treatment period, the rats were anesthetized and weighed. While still under anesthetic, the rats were sacrificed by exsanguination. The femurs, tibiae and spine were excised and placed in prelabeled tubes. The bones were immediately placed on dry ice and later stored at −70° C. FIG. 2 shows the experimental design summary and timeline.

Dual Energy X-Ray Absorptiometry (DEXA)

Dual Energy X-ray Absorptiometry (DEXA) is used to measure bone mineral content (BMC) and calculate bone mineral density (BMD). DEXA is performed using a PIXImus Densitometer (Lunar GE Corp., Madison, Wis., U.S.A), which is designed specifically for measurement of small animals. Measurements are taken by exposing a sample to a cone shaped beam of both high and low energy x-rays. The low energy beam pass through soft tissue but not bone, whereas the high energy beam pass through all material. The bone density is calculated based on the energy absorbed by the bone from the high and low energy beams. The machine is calibrated before each use using an aluminum/lucite phantom placed one centimeter from the back of the PIXImus scanning area.

Excised and cleaned femur and lumbar vertebrae 4 and 5 were scanned. The samples were individually placed, semi-frozen on a specialized plate made of polystyrene to simulate equivalent soft tissue thickness on bone. All samples were placed in the same orientation for each measurement. The BMD of lumbar vertebrae L4 and L5 were added together for overall analysis.

Software supplied by the manufacturer was used to calculate the BMD from the BMC and area [BMD(g/cm2)=BMC (g)/area (cm2)]. The area was manually defined by sizing a box around the sample termed, the region of interest (ROI).

Statistical Analysis

All data is displayed as the mean, +/−standard error of mean (SEM). Statistical analysis was performed using statistical software, SPSS (version 10.0).

Comparisons involving two groups were analyzed by independent t-test. For multiple comparisons, the Levene's test of homgeneity of variance was performed as a test for equal variance. If the data had equal variance, multiple comparisons were analyzed by one-way ANOVA analysis using the pairwise comparison Protected Fisher's Least Significant Difference (LSD) post hoc test. Significance was assigned at p<0.05 and a trend assigned at p<0.1.

Dual Energy X-Ray Absorptiometry (DEXA)

DEXA is used to calculate the Bone Mineral Density (BMD). The BMD of lumbar vertebrae are mainly used to determine changes in trabecular bone mass, while excised femurs are used mainly to determine changes in cortical bone mass.

Effect of Ovariectomy

The effect of ovariectomy on bone mineral density was examined to confirm the estrogen-deficiency model for postmenopausal osteoporosis. T-test analysis revealed there was a significant decrease in BMD of the lumbar vertebrae in the OVX group compared to the BMD of the control Sham group (p=0.02), shown in FIG. 4a. This effect also occurred in the femur as shown in FIG. 4b, where again there was a significant decrease in BMD of the OVX group compared to the sham (p=0.046). This confirms that the OVX model is functional in this study.

Effect of AOD Treatment

Figure 5:
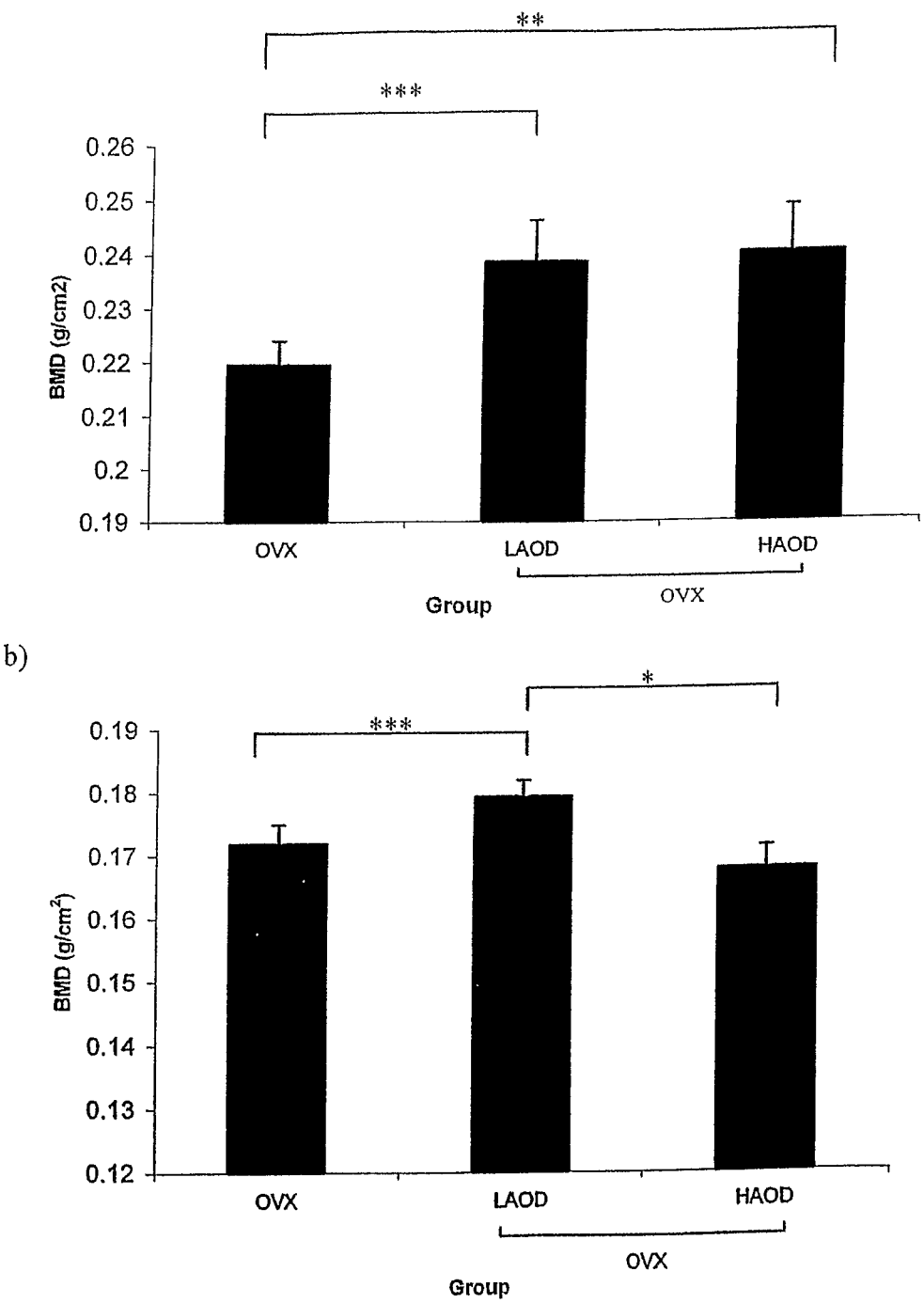
FIG. 5: BMD of a) lumbar vertebrae (L4+L5) (OVX to LAOD 0.075, 0.05 and b) femur (0.1, 0.01), comparing OVX control with drug treatment groups (*significance assigned at $p<0.01$, significance assigned at $p<0.05$, *trend assigned at $p<0.1$).

The BMD change in response to AOD differs between the lumbar vertebrae and the femur. In the lumbar vertebrae ANOVA analysis indicated that both the high dose (p=0.05) and low dose (p=0.076) of AOD increased BMD significantly compared to the OVX control as shown in FIG. 5a. The BMD was returned to that of the sham control levels.

There was a trend for femoral BMD to increase with the low dose of AOD (p=0.107) but this effect was not seen with the high dose of AOD as shown in FIG. 5b. The high dose of AOD did not produce any increase in BMD and had a similar BMD to the OVX control group. The BMD of the high dose AOD group was significantly lower than the low dose AOD group (p=0.013).

Overall, there was an increase in BMD in the lumbar vertebrae and femur with treatment of AOD, but there was a more significant increase in the lumbar vertebrae.

Example 3

Mechanical Testing Methods

Three tests were completed to determine the mechanical properties of both cortical and trabecular bone. Three point bending and torsion tests were completed to examine the mechanical and material properties of cortical bone. Vertebral compression was completed to investigate the mechanical and material properties of trabecular bone.

Statistical Analysis

All data is displayed as the mean, +/−standard error of mean (SEM). Statistical analysis was performed using statistical software, SPSS (version 11.0). Comparisons involving two groups were analyzed by independent student's t-test. Multiple comparisons were analyzed by one-way ANOVA analysis using the pairwise comparison Protected Fisher's Least Significant Difference (LSD) post hoc test. Significance was assigned at p<0.05 and a trend assigned at p<0.1.

Three-Point Bending

The right femur was used for the three point bending test. The bones to be tested were transferred from a −70° C. to a −20° C. freezer two days before testing. The night before testing, the samples were removed from the −20EC freezer and individually wrapped in gauze soaked in saline solution. These samples were then placed at approximately 4° C. overnight to ensure the samples were completely thawed. Before testing, the bones were measured to determine the placement of the sample on the jig. First, the length of the bone was measured with digital calipers. From the distal end of the femur, a mark was placed on the bone at 25% of the entire length. From the first point, a second mark was placed at 15.6 mm, the set gauge length, and finally a mark was placed at the midpoint of the gauge length.

Testing was completed on a mechanical testing machine (Instron 4465, Instron Canada Inc., Toronto, ON, Canada) using a 1000 Newton load cell. The load cell was calibrated and balanced after the three-point bending jig was installed. The stainless steel jig used for testing consisting of a base with two supports and an indentor that was attached to the crosshead of the Instron. All the samples were placed in the same orientation, with the anterior side facing upwards, resting naturally on the supports in their most stable position. The gauge length marks were aligned with the 2 supports of the jig and the indentor was aligned with the mid point of the gauge length. The bones were preloaded with approximately 1.0 N. The test was run at a speed of 1 mm/min until failure. Load versus time data was acquired from the Instron by LabView data acquisition software (National Instruments Corp.; Austin, Tex.). Digital images were taken of the cross-section of the femur at the breakpoint (Nikon 8500, Nikon Canada). Image analysis software (ImageJ 1.28u, National Institute of Health) was used to determine dimensions of the bone as well as to calculate the moment of inertia. Diameters in the medial-lateral (M/L) and anterior/posterior(A/P) directions were measured as well as the thickness.

Time data was converted into deformation data to construct a load-deformation curve using spreadsheet software (Excel2000, Microsoft). From this curve the non-normalized mechanical properties were determined; including the ultimate load, failure deformation point, the energy to failure (area under the curve) and stiffness (slope of linear region).

The diameter and moment of inertia were used to convert the load-deformation curve into a stress-strain curve. Normalized mechanical properties taken from the stress/strain curve included ultimate stress, failure strain, normalized energy to failure an elastic modulus.

Vertebral Compression

The 5th Lumbar vertebra (L5) was used for compression testing. The vertebrae were trimmed of all processes, leaving only the vertebral body for testing. The bones to be tested were removed from the −70° C. freezer and placed in the −20° C. freezer at least one day before testing. The samples were removed from the −20° C. freezer at least two hours before testing to ensure the bones were completely defrosted. The vertebrae were individually wrapped in gauze soaked in saline solution during defrosting.

Digital images were taken and image analysis software (ImageJ 1.28u, NIH) was used to determine the height and cross-sectional area of the vertebral body. Compression testing was completed on a mechanical testing machine (Instron 4465, Instron Canada) using a 1000N load cell. The vertebral bodies were positioned in the shallow well of the jig with the caudal or flat end down. Samples were secured with 3 screws and then surrounded with PMMA. The vertebrae were covered in saline-soaked gauze while the PMMA set for at least 10 minutes. A small amount of PMMA was used to even out the loading surface of the vertebrae. The samples were preloaded with approximately 1.0 N and left for approximately 3 minutes for the PMMA to set. While preloading the samples, the distance between the platens was measured using digital calipers. The gauge length was then determined by subtracting the height of the jig with the distance between the platens. The bone was loaded at 1.0 mm/min until failure. Failure for vertebral compression was defined as an obvious drop in force or in less defined instances, a 10% drop in force.

Load versus time data was acquired from the Instron by LabView data acquisition software. Digital images were taken to determine the height and cross-sectional area, using image analysis software (ImageJ, NIH).

Time was converted into deformation data to construct a load-deformation curve. From this curve non-normalized mechanical properties were determined including, the ultimate load, failure deformation point, the energy to failure (area under the curve) and stiffness (slope of linear region). Cross-sectional area taken from the digital image and gauge length were used to convert the load-deformation curve into a stress-strain curve. Normalized properties taken from the stress-strain curve included, ultimate stress, failure strain, the normalized energy to failure (area under the curve) and elastic modulus (slope).

Femoral Neck Fracture

The right proximal femur was used for femoral neck fracture testing. Before testing, X-rays were taken of the proximal femur, ensuring that the femoral head was flat against the film. The bones to be tested were removed from a −20° C. freezer and individually wrapped in gauze soaked in saline solution. These samples were then left at room temperature, approximately 21° C., for 2 hours to ensure the samples were completely thawed. Any connective tissue surrounding the femoral neck was removed before testing.

Testing was completed on the Instron 4464. Samples were secured into the jig using 4 flat-ended screws. The sample was visually aligned so that the long axis was perpendicular to the jig well and had a gauge length (from the end of the bone to the top of the jig well) of approximately 11 mm. The well of the jig was then filled with PMMA and allowed to set for 10 minutes. The sample was covered in saline-soaked gauze while setting. Before testing, digital calipers were used to measure the exact gauge length and the diameter of the femoral neck in the medial/lateral direction and anterior/posterior direction. Once the sample was set and measurements taken, it was loaded into the Instron machine and the femoral neck was aligned with the edge of the hole drilled into the bottom plate. A preload of approximately 1.0 N was applied. The test was run at 2.5 mm/min until failure.

Time was converted into deformation data to construct a load-deformation curve. From this curve non-normalized mechanical properties were determined including, the ultimate load, failure deformation point, the energy to failure (area under the curve) and stiffness (slope of linear region). These mechanical properties were compared directly without any normalization due to the complex geometry of the femoral neck and the combination of different loads (compressive force, shear force and bending force) applied to the sample.

Mechanical Testing Results

Non-normalized mechanical properties were taken from the load displacement curve generated in the three-point bending, torsion and vertebral compression tests. This data was normalized using geometric parameters. Normalized parameters were compared for significant differences. If problems occurred while testing the bone, these tests were excluded from the analyses. One sample from the HAOD group had an abnormal callus on the right femur and was not tested. Outlying data discovered with statistical testing was excluded from the following analyses.

Three Point Bending

Figure 6:
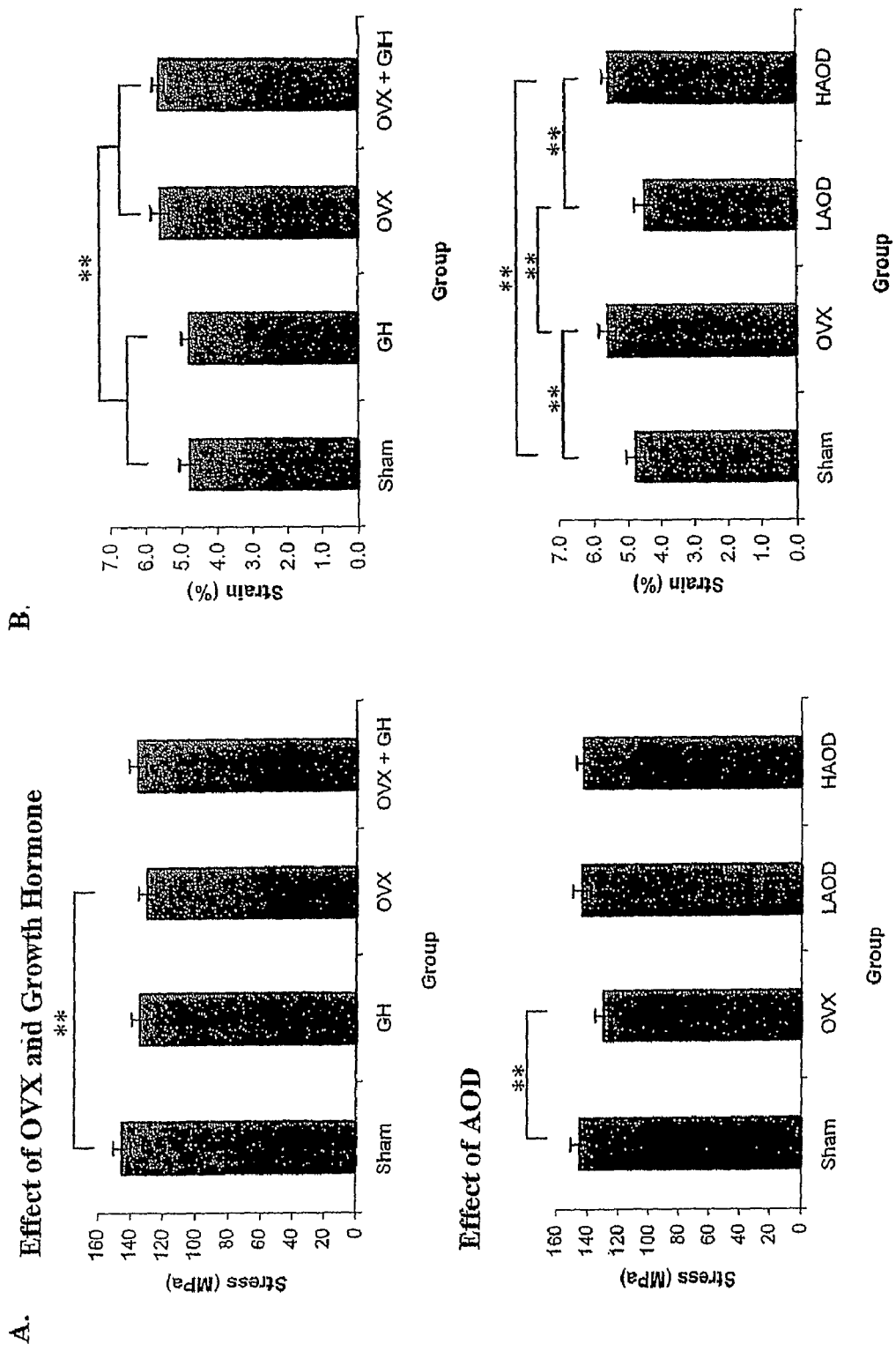
FIG. 6: Three-point bending results for right femur comparing all treatment groups A) Ultimate Stress B) Failure Strain (* indicates significance at $p<0.01$. ** indicates significance at $p<0.05$).
Figure 7:
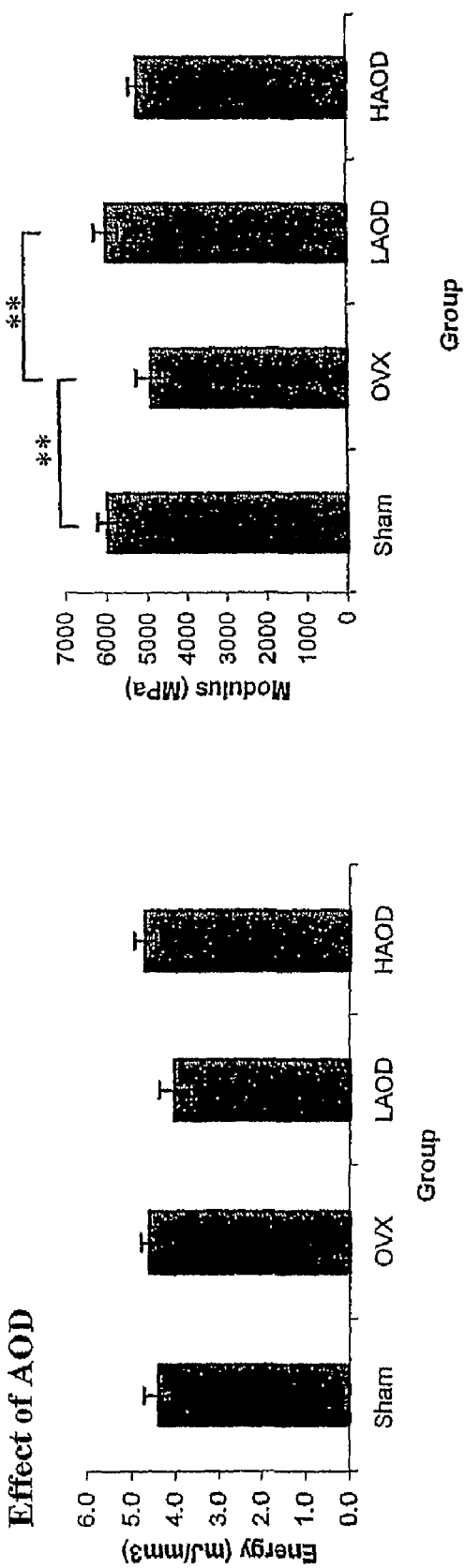
FIG. 7: Three-point bending results for right femur comparing all treatment groups A) Normalized Energy to failure B) Elastic Modulus (* indicates significance at $p<0.01$. ** indicates significance at $p<0.05$).

The three point bending test was performed on the femur and represents mechanical properties of cortical bone. Graphs showing group data for ultimate stress, failure strain, energy to failure and elastic modulus can be seen in FIGS. 6 and 7.

Effect of AOD Treatment

AOD treatment, both low (LAOD) and high dose (HAOD), showed no significant difference in ultimate stress, although trends were seen that indicate that the LAOD and HAOD groups had a higher ultimate stress compared to the OVX control group ($p=0.062$, $p=0.076$). The HAOD group and OVX had similar strains and elastic modulus, but the LAOD group had a higher elastic modulus ($p=0.014$) and lower failure strain ($p=0.005$). See FIG. 6 and FIG. 7.

Summary

The OVX model was shown to be functional by the decrease in cortical bone strength and stiffness compared to sham. A differential effect was seen between the low dose and the high dose of AOD drug treatment. Both doses increased the strength compared to OVX but the low dose was more effective and also increased the stiffness.

Vertebral Compression

Vertebral compression testing was performed on the 5th lumbar vertebral body and represents mechanical properties of trabecular bone. A few vertebrae that had their processes trimmed too close to the vertebral body had compromised cortical shells and therefore were excluded from the analyses.

Effect of AOD Treatment

Figure 8:
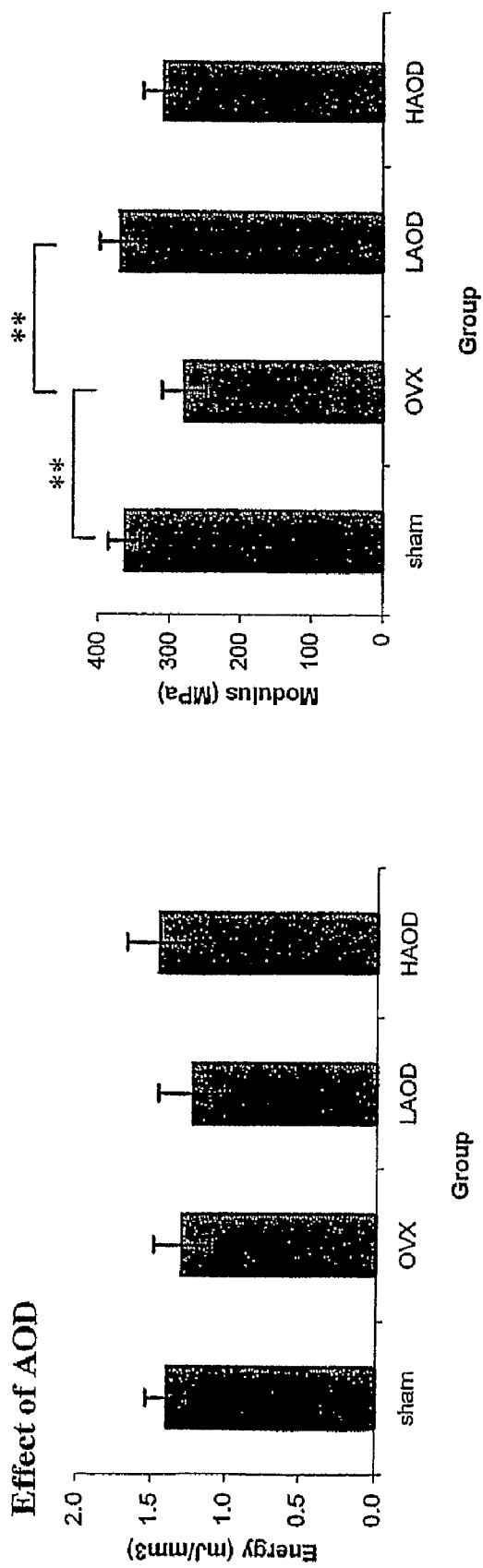
FIG. 8: Vertebral compression of L5 comparing all treatment groups A) Normalized Energy to Failure B) Elastic Modulus (** indicates significance at $p<0.05$).

The LAOD group had a higher elastic modulus than the OVX control ($p=0.05$). See FIG. 8.

Summary

Treatment with the low dose of AOD showed a trend of increased stiffness compared to OVX represented by an increase in elastic modulus. Estrogen treatment did not prevent a decrease in strength and stiffness caused by OVX although the stress and elastic modulus values were higher. Overall there is less of an effect of AOD on trabecular bone compared to cortical bone. This would indicate that AOD has a similar effect on the skeleton as intact GH. GH is known it increase cortical bone formation at the periosteal surface.

Femoral Neck Fracture

Effect of AOD

Figure 9:
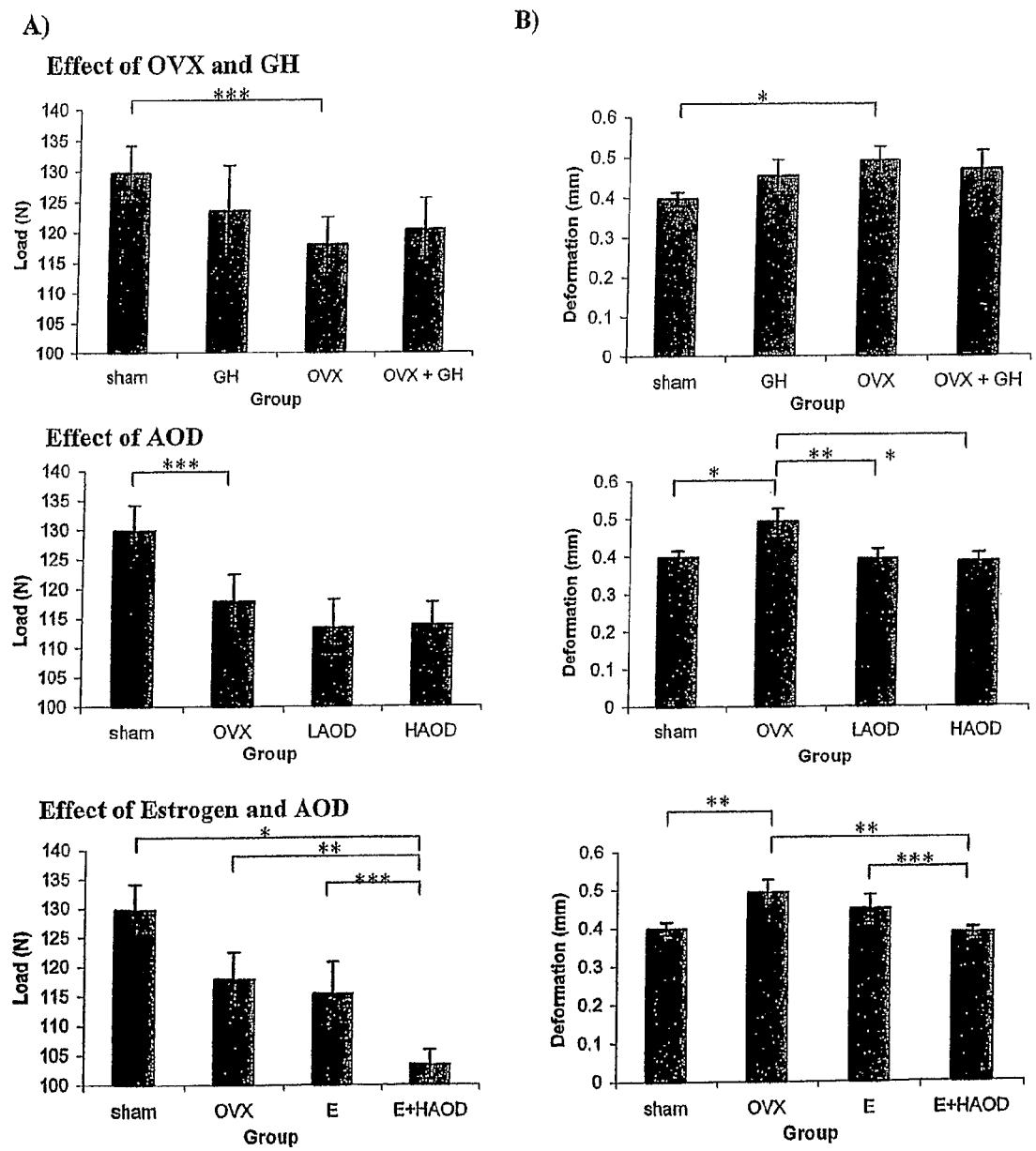
FIG. 9: Mechanical Properties of the Femoral Neck A) Ultimate Load (N) B) Failure Deformation (mm). * represents significance $p<0.01$,  represents significance $p<0.05$, * represents trend of $p<0.1$.
Figure 10:
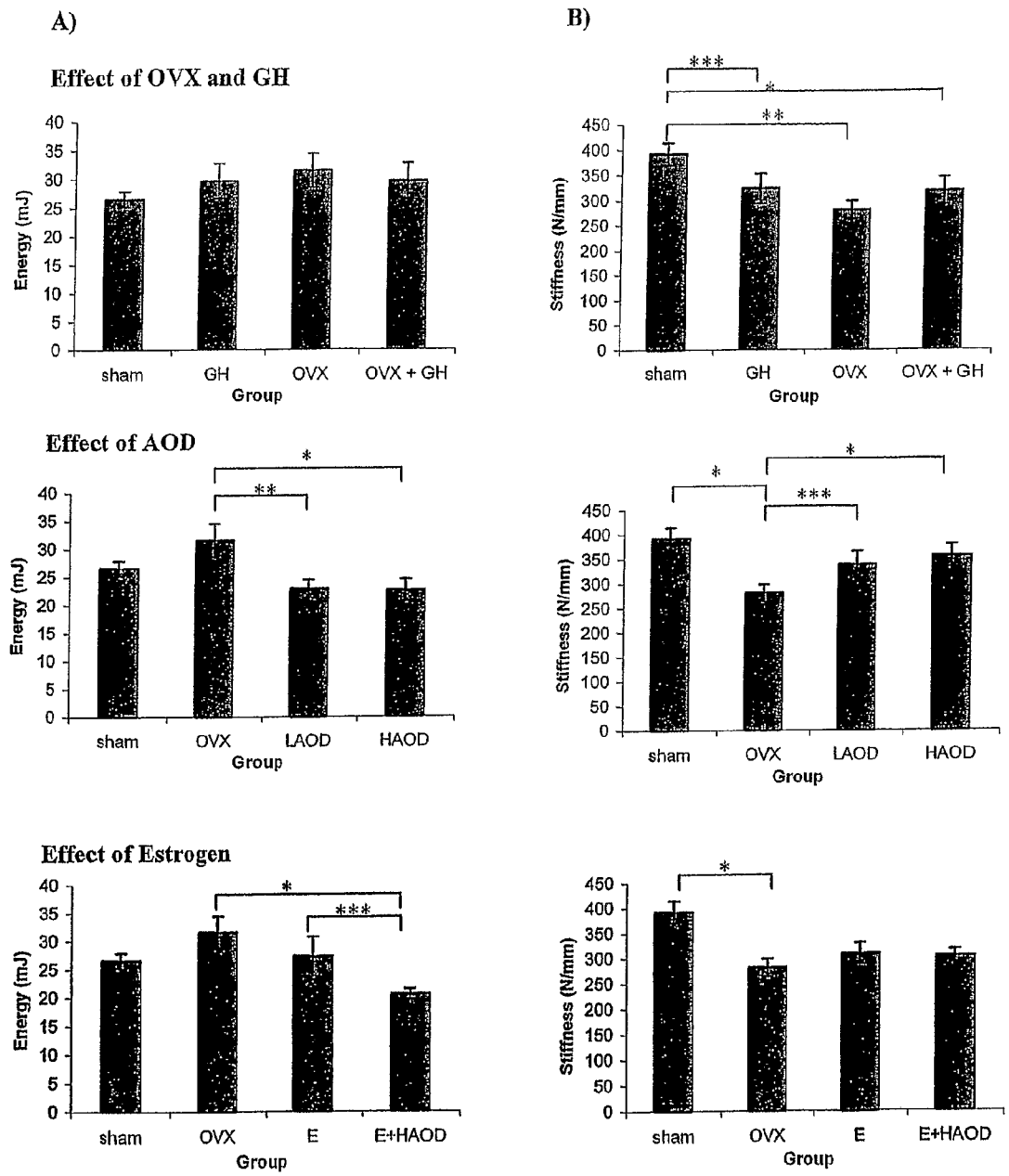
FIG. 10: Mechanical Properties of the Femoral Neck A) Energy to Failure (mJ) B) Stiffness (MPa)* represents significance $p<0.01$,  represents significance $p<0.05$, * represents trend of $p<0.1$.

AOD influenced femoral neck deformation and stiffness. OVX rats had significantly higher deformation than both the low dose AOD and high dose AOD groups (0.017, 0.009). Both AOD groups had a higher stiffness than OVX ($p=0.092$, $p=0.023$) but there was only a significant difference with the HAOD group. The OVX group had a significantly higher energy to failure due to the higher ductility ($p=0.013$, $p=0.008$). There was an increase in stiffness in the AOD treated groups that may indicate that the decline in bone quality that occurs in the OVX rats may have been prevented. See FIG. 9 and FIG. 10.

Summary

Ovariectomy caused a decrease in femoral neck strength and stiffness. This is mainly due to loss of trabecular bone in the femoral neck. This again reaffirms that the OVX model is functional. Treatment with the low dose and high dose AOD showed a trend of increased stiffness compared to OVX but no difference in strength. This could be due to material changes such as changes in the mineral or collagen.

DISCUSSION

We hypothesized that AOD would not prevent the skeletal changes that result from ovariectomy and therefore would not have an effect on bone metabolism. The results of this study suggest our hypothesis was incorrect and that AOD does have an effect on the skeleton. This was seen throughout the study by the prevention of many skeletal changes that occur with ovariectomy. It was thought that the AOD 9604 peptide contained only the domain that would stimulate lipolysis but would not stimulate bone metabolism. We believe that since intact GH has several different target cells within the body that it is plausible that AOD interacts with bone cells.

AOD had effects on both trabecular and cortical bone but primarily affected cortical bone. It is thought that AOD has similar effects in the skeleton as the intact GH molecule. AOD also prevented the decline of cortical BMD and mechanical test showed that low dose of AOD prevented cortical bone weakening. There was little effect of AOD on trabecular bone.

APPENDIX 1

Mouse IGF-I

Catalog Number: DY791

This DuoSet ELISA Development kit contains the basic components required for the development of sandwich ELISAs to measure natural and recombinant mouse Insulin-like Growth Factor (IGF-I) in cell culture supernates and serum.[i] Each kit contains sufficient materials to run ELISAs on approximately fifteen 96-well plates, provided that the following conditions are met:[ii]

[i] For assaying serum samples, each laboratory should develop and validate its own serum diluent. The serum diluent must not be used to dilute the Detection Antibody or the Streptavidin-HRP.
[ii] Individual results may vary due to differences in technique, plasticware and water sources.

The assay is run as summarized in the General ELISA protocol.
The recommended microplates, buffers, diluents, substrates, and solutions are used.
This package insert must be read in its entirety before using this product.

Materials Provided

Bring all reagents to room temperature before use.

Capture Antibody (Part 841413, 1 vial)—720 µg/mL of hamster anti-mouse IGF-I when reconstituted with 1.0 mL of PBS. After reconstitution, store at 2-8° C. for up to 60 days or aliquot and store at −20° C. to −70° C. in a manual defrost freezer for up. to 6 months.[iii] Dilute to a working concentration of 4.0 µg/mL in PBS,[iv] without carrier protein.

[iii] Provided this is within the expiration date of the kit.
[iv] Allow all components to sit for a minimum of 15 minutes with gentle agitation after initial reconstitution. Working dilutions should be prepared and used immediately.

Detection Antibody (Part 841414, 1 vial)—36 µg/mL of biotinylated goat anti-mouse IGF-I when reconstituted with 10 mL of Reagent Diluent (see Solutions Required section). After reconstitution, store at 2-8° C. for up to 60 days or aliquot and store at −20° C. to −70° C. in a manual defrost freezer for up to 6 months.[3] Dilute to a working concentration of 200 ng/mL in Reagent Diluent.[4]

Standard (Part 841415, 1 vial)—100 ng/mL of recombinant mouse IGF-I when reconstituted with 0.5 mL of Reagent Diluent (see Solutions Required section). Allow the standard to sit for a minimum of 15 minutes with gentle agitation prior to making dilutions. Store reconstituted standard at 2-8° C. for up to 60 days or aliquot and store at −70° C. for up to 6 months.[3] A seven point standard curve using 2-fold serial dilutions in Reagent Diluent, and a high standard of 2000 pg/mL is recommended.

Streptavidin-HRP (Part 890803, 1 vial)—1.0 mL of streptavidin conjugated to horseradish-peroxidase. After initial use store at 2-8° C. for up to 6 months.[3] DO NOT FREEZE. Dilute to the working concentration specified on the vial label using Reagent Diluent (see Solutions Required section).[4]

Solutions Required

PBS—137 mM NaCl, 2.7 mM KCl, 8.1 mM $Na_2HPO_4$, 1.5 mM $KH_2PO_4$, pH 7.2-7.4, 0.2 µm filtered.
Wash Buffer—0.05% Tween® 20 in PBS, pH 7.2-7.4 (R&D Systems Catalog # WA126).
Block Buffer—5% Tween 20 in PBS with 0.05% $NaN_3$.
Reagent Diluent[1]—5% Tween 20 in PBS, pH 7.2-7.4, 0.2 µm filtered.
Substrate Solution—1:1 mixture of Color Reagent A ($H_2O_2$) and Color Reagent B (Tetramethylbenzidine) (R&D Systems Catalog #DY999).
Stop Solution—2 N $H_2SO_4$ (R&D Systems Catalog #DY994).

General ELISA Protocol

Plate Preparation

1. Dilute the Capture Antibody to the working concentration in PBS without carrier protein. Immediately coat a 96-well microplate[v] with 100 µL per well of the diluted Capture Antibody. Seal the plate and incubate overnight at room temperature.

[v] Costar EIA Plate (Cat. # 2592) is suggested.

2. Aspirate each well and wash with Wash Buffer, repeating the process two times for a total of three washes. Wash by filling each well with Wash Buffer (400 µL); using a squirt bottle, manifold dispenser or autowasher. Complete removal of liquid at each step is essential for good performance. After the last wash; remove any remaining Wash Buffer by aspirating or by inverting the plate and blotting it against clean paper towels.
3. Block plates by adding 300 µL of Block Buffer to each well. Incubate at room temperature for a minimum of 1 hour.
4. Repeat the aspiration/wash as in step 2. The plates are now ready for sample addition.

Assay Procedure

1. Add 100 µL of sample or standards in Reagent Diluent, or an appropriate diluent, per well. Cover with an adhesive strip and incubate 2 hours at room temperature.
2. Repeat the aspiration/wash as in step 2 of Plate Preparation.
3. Add 100 µL of the Detection Antibody, diluted in Reagent Diluent, to each well. Cover with a new adhesive strip and incubate 2 hours at room temperature.
4. Repeat the aspiration/wash as in step 2 of Plate Preparation.
5. Add 100 µL of the working dilution of Streptavidin-HRP to each well. Cover the plate and incubate for 20 minutes at room temperature. Avoid placing the plate in direct light.
6. Repeat the aspiration/wash as in step 2.
7. Add 100 µL of Substrate Solution to each well. Incubate for 20 minutes at room temperature. Avoid placing the plate in direct light.
8. Add 50 µL of Stop Solution to each well. Gently tap the plate to ensure thorough mixing.
9. Determine the optical density of each well immediately, using a microplate reader set to 450 nm. If wavelength correction is available, set to −540 nm or 570 nm. If wavelength correction is not available, subtract readings at 540 nm or 570 nm from the readings at 450 nm. This subtraction will correct for optical imperfections in the plate. Readings made directly at 450 nm without correction may be higher and less accurate.

Technical Hints and Limitations

This DuoSet should not be used beyond the expiration date on the label.

It is important that the diluents selected for reconstitution and for dilution of the standard reflect the environment of the samples being measured. The diluent suggested in this protocol should be suitable for most cell culture supernate samples. Validate diluents for specific sample types prior to use.

The type of enzyme and substrate and the concentrations of capture/detection antibodies used can be varied to create an immunoassay with a different sensitivity and dynamic range. A basic understanding of immunoassay development is required for the successful use of these reagents in immunoassays.

A thorough and consistent wash technique is essential for proper assay performance. Wash Buffer should be dispensed forcefully and removed completely from the wells by aspiration or decanting. Remove any remaining Wash Buffer by inverting the plate and blotting it against clean paper towels.

Use a fresh reagent reservoir and pipette tips for each step.
It is recommended that all standards and samples be assayed in duplicate.

Avoid microbial contamination of reagents and buffers. This may interfere with the sensitivity of the assay. Buffers containing a large quantity of protein should be made under sterile conditions and stored at 2-8° C. or be prepared fresh daily.

Precautions

The Stop Solution suggested for use with this kit is an acid solution. Wear eye, hand, face, and clothing protection when using this material.

Calculation of Results

Average the duplicate readings for each standard, control, and sample and subtract the average zero standard optical. density.

Create a standard curve by reducing the data using computer software capable of generating a four parameter logistic (4-PL) curve-fit. As an alternative, construct a standard curve by plotting the mean absorbance for each standard on the y-axis against the concentration on the x-axis and draw a best fit curve through the points on the graph. The data may be linearized by plotting the log of the IGF-1 concentrations versus the log of the O.D. and the best fit line can be determined by regression analysis. This procedure will produce an adequate but less precise fit of the data. If samples have been diluted, the concentration read from the standard curve must be multiplied by the dilution factor.

Typical Data

This standard curve is only for demonstration purposes. A standard curve should be generated for each set of samples assayed.

Figure 11:
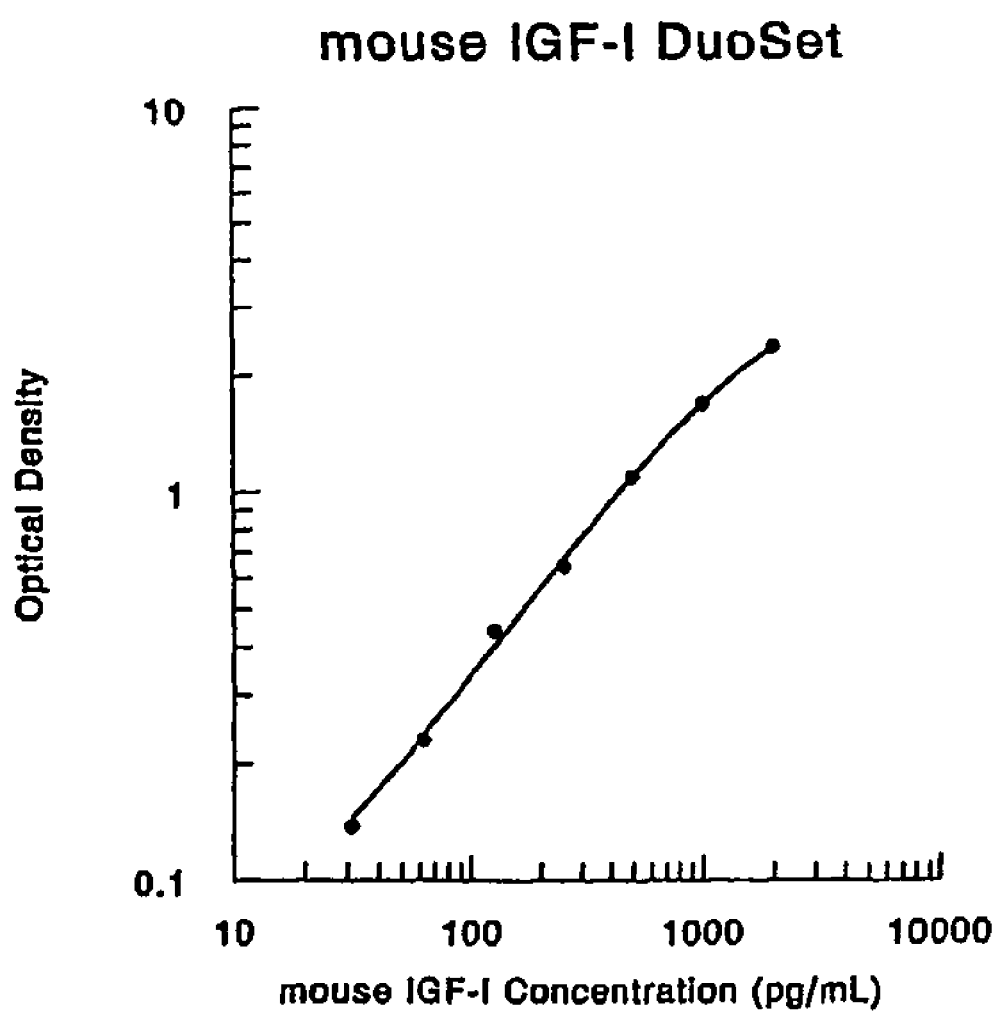
FIG. 11: Typical data generated when using the mouse IGF-I DuoSet kit. The standard curve was calculated using a computer generated 4-PL curve-fit.

FIG. 11 represents typical data generated when using this mouse IGF-I DuoSet. The standard curve was calculated using a computer generated 4-PL curve-fit.

Specificity

A sample containing 50 ng/mL of recombinant mouse IGF-II was assayed and exhibited no cross-reactivity or interference.

A sample containing 25 ng/mL of recombinant human IGF-I reads as 63 pg/mL (0.2% cross-reactivity).

Calibration

This DuoSet is calibrated against a highly purified, *E. coli*-expressed recombinant mouse IGF-I produced at R&D Systems.

| R&D Systems, Inc. | R&D Systems Europe, Ltd. |
|---|---|
| 614 McKinley Place NE | 19 Barton Lane |
| Minneapolis, MN 55413 | Abingdon Science Park |
| USA | Abingdon, OX14 3NB |
| 1-800-343-7475 | United Kingdom |
| Tel: (612) 379-2956 | Tel: +44 (0) 1235 529449 |
| Fax: (612) 656-4400 | Fax: +44 (0) 1235 533420 |

The invention claimed is:

1. A method of treating a bone disorder in a mammal, increasing bone mass density in a mammal, or increasing osteoblast formation in a mammal, comprising administering to the mammal a therapeutically effective amount of a peptide that is up to 50 amino acid residues in length and that comprises (a) amino acid residues 177-191 of human growth hormone or (b) any of SEQ ID NOS: 1-22.

2. A method according to claim 1, wherein the peptide reduces lipogenic activity and/or stimulates lipolysis.

3. The method of claim 1, wherein the peptide comprises at least the disulphide-bonded loop of a mammalian growth hormone.

4. The method of claim 1, wherein the peptide is up to 20 amino acids in length and comprises an amino acid sequence selected from any of SEQ ID NOS: 1-22.

5. The method of claim 1, wherein the peptide comprises amino acids 177-191 of human growth hormone (hGH 177-191).

6. The method of claim 1, wherein the peptide consists of SEQ ID NO: 7.

7. The method of claim 1, wherein the peptide is administered orally, sublingually, buccally, intranasally, by inhalation, transdermally, topically, or parenterally, by subcutaneous, intraveneous, intramuscular, intrathecal, intracranial, injection or infusion techniques.

8. The method of claim 1, wherein the bone disorder is characterized by altered bone metabolism.

9. The method of claim 1, wherein the bone disorder is selected from the group consisting of: osteoporosis, postmenopausal osteoporosis, osteopenia, Paget's disease, osteolytic metastasis in cancer patients, osteodistrophy in liver disease, altered bone metabolism caused by renal failure or haemodialysis, altered bone metabolism cause by bone fracture, altered bone metabolism caused by bone surgery, altered bone metabolism caused by aging, altered bone metabolism caused by pregnancy, and altered bone metabolism caused by malnutrition.

10. The method of claim 1, wherein the mammal is a human.

11. The method of claim 1, wherein the peptide consists essentially of amino acids residues 177-191 of human growth hormone.

12. The method of claim 1, wherein the amino acid sequence of the peptide consists of any one of SEQ ID NOS: 1-22.

13. A method of treating a bone disorder in a mammal, increasing bone mass density in a mammal, or increasing osteoblast formation in a mammal, comprising administering to the mammal a pharmaceutical composition that comprises a pharmaceutically acceptable carrier in combination with a therapeutically effective amount of a peptide that is up to 50 amino acid residues in length and that comprises (a) amino acid residues 177-191 of human growth hormone or (b) any of SEQ ID NOS:1-22.

* * * * *

SEQUENCE LISTING

```
<160> NUMBER OF SEQ ID NOS: 22

<210> SEQ ID NO 1
<211> LENGTH: 15
<212> TYPE: PRT
<213> ORGANISM: Artificial
<220> FEATURE:
<223> OTHER INFORMATION: hGH 177 - 191 with Penicillamine at 182 and
      189; cyclic peptide
<220> FEATURE:
<221> NAME/KEY: Xaa
<222> LOCATION: (6)..(6)
<223> OTHER INFORMATION: Penicillamine
<220> FEATURE:
<221> NAME/KEY: DISULFID
<222> LOCATION: (6)..(13)
<220> FEATURE:
<221> NAME/KEY: Xaa
<222> LOCATION: (13)..(13)
<223> OTHER INFORMATION: Penicillamine

<400> SEQUENCE: 1

Leu Arg Ile Val Gln Xaa Arg Ser Val Glu Gly Ser Xaa Gly Phe
1               5                   10                  15

<210> SEQ ID NO 2
<211> LENGTH: 15
<212> TYPE: PRT
<213> ORGANISM: Artificial
<220> FEATURE:
<223> OTHER INFORMATION: hGH 177 - 191 with CH3CO replacing NH2; cyclic
      peptide
<220> FEATURE:
<221> NAME/KEY: MOD_RES
<222> LOCATION: (1)..(1)
```

```
<223> OTHER INFORMATION: CH3CO replaces NH2
<220> FEATURE:
<221> NAME/KEY: DISULFID
<222> LOCATION: (6)..(13)

<400> SEQUENCE: 2

Leu Arg Ile Val Gln Cys Arg Ser Val Glu Gly Ser Cys Gly Phe
1               5                   10                  15

<210> SEQ ID NO 3
<211> LENGTH: 15
<212> TYPE: PRT
<213> ORGANISM: Artificial
<220> FEATURE:
<223> OTHER INFORMATION: hGH 177 - 191 with H replacing NH2; cyclic
      peptide
<220> FEATURE:
<221> NAME/KEY: MOD_RES
<222> LOCATION: (1)..(1)
<223> OTHER INFORMATION: H replaces NH2
<220> FEATURE:
<221> NAME/KEY: DISULFID
<222> LOCATION: (6)..(13)

<400> SEQUENCE: 3

Leu Arg Ile Val Gln Cys Arg Ser Val Glu Gly Ser Cys Gly Phe
1               5                   10                  15

<210> SEQ ID NO 4
<211> LENGTH: 15
<212> TYPE: PRT
<213> ORGANISM: Artificial
<220> FEATURE:
<223> OTHER INFORMATION: hGH 177 - 191 with CONH2 replacing COOH; cyclic
      peptide
<220> FEATURE:
<221> NAME/KEY: DISULFID
<222> LOCATION: (6)..(13)
<220> FEATURE:
<221> NAME/KEY: MOD_RES
<222> LOCATION: (15)..(15)
<223> OTHER INFORMATION: CONH2 replaces COOH

<400> SEQUENCE: 4

Leu Arg Ile Val Gln Cys Arg Ser Val Glu Gly Ser Cys Gly Phe
1               5                   10                  15

<210> SEQ ID NO 5
<211> LENGTH: 15
<212> TYPE: PRT
<213> ORGANISM: Artificial
<220> FEATURE:
<223> OTHER INFORMATION: hGH 177 - 191 with Lysine at 183; cyclic
      peptide
<220> FEATURE:
<221> NAME/KEY: DISULFID
<222> LOCATION: (6)..(13)

<400> SEQUENCE: 5

Leu Arg Ile Val Gln Cys Lys Ser Val Glu Gly Ser Cys Gly Phe
1               5                   10                  15

<210> SEQ ID NO 6
<211> LENGTH: 15
<212> TYPE: PRT
<213> ORGANISM: Artificial
<220> FEATURE:
<223> OTHER INFORMATION: hGH 177-191 with Lysine at 183 and amide bond
      between 183 and 186; cyclic peptide
<220> FEATURE:
<221> NAME/KEY: DISULFID
<222> LOCATION: (6)..(13)
```

```
<220> FEATURE:
<221> NAME/KEY: MISC_FEATURE
<222> LOCATION: (7)..(10)
<223> OTHER INFORMATION: Amide bond

<400> SEQUENCE: 6

Leu Arg Ile Val Gln Cys Lys Ser Val Glu Gly Ser Cys Gly Phe
1               5                   10                  15

<210> SEQ ID NO 7
<211> LENGTH: 16
<212> TYPE: PRT
<213> ORGANISM: Artificial
<220> FEATURE:
<223> OTHER INFORMATION: Tyrosine - hGH 177-191; cyclic peptide
<220> FEATURE:
<221> NAME/KEY: DISULFID
<222> LOCATION: (7)..(14)

<400> SEQUENCE: 7

Tyr Leu Arg Ile Val Gln Cys Arg Ser Val Glu Gly Ser Cys Gly Phe
1               5                   10                  15

<210> SEQ ID NO 8
<211> LENGTH: 16
<212> TYPE: PRT
<213> ORGANISM: Artificial
<220> FEATURE:
<223> OTHER INFORMATION: Lysine - hGH 177-191; cyclic peptide
<220> FEATURE:
<221> NAME/KEY: DISULFID
<222> LOCATION: (7)..(14)

<400> SEQUENCE: 8

Lys Leu Arg Ile Val Gln Cys Arg Ser Val Glu Gly Ser Cys Gly Phe
1               5                   10                  15

<210> SEQ ID NO 9
<211> LENGTH: 17
<212> TYPE: PRT
<213> ORGANISM: Artificial
<220> FEATURE:
<223> OTHER INFORMATION: Lysine - Lysine - hGH 177-191; cyclic peptide
<220> FEATURE:
<221> NAME/KEY: DISULFID
<222> LOCATION: (8)..(15)

<400> SEQUENCE: 9

Lys Lys Leu Arg Ile Val Gln Cys Arg Ser Val Glu Gly Ser Cys Gly
1               5                   10                  15

Phe

<210> SEQ ID NO 10
<211> LENGTH: 15
<212> TYPE: PRT
<213> ORGANISM: Artificial
<220> FEATURE:
<223> OTHER INFORMATION: hGH 177 - 191 with Alanine at 177; cyclic
      peptide
<220> FEATURE:
<221> NAME/KEY: DISULFID
<222> LOCATION: (6)..(13)

<400> SEQUENCE: 10

Ala Arg Ile Val Gln Cys Arg Ser Val Glu Gly Ser Cys Gly Phe
1               5                   10                  15

<210> SEQ ID NO 11
<211> LENGTH: 15
```

```
<212> TYPE: PRT
<213> ORGANISM: Artificial
<220> FEATURE:
<223> OTHER INFORMATION: hGH 177 - 191 with Lysine at 178; cyclic
      peptide
<220> FEATURE:
<221> NAME/KEY: DISULFID
<222> LOCATION: (6)..(13)

<400> SEQUENCE: 11

Leu Lys Ile Val Gln Cys Arg Ser Val Glu Gly Ser Cys Gly Phe
1               5                   10                  15

<210> SEQ ID NO 12
<211> LENGTH: 15
<212> TYPE: PRT
<213> ORGANISM: Artificial
<220> FEATURE:
<223> OTHER INFORMATION: hGH 177 - 191 with Alanine at 179; cyclic
      peptide
<220> FEATURE:
<221> NAME/KEY: DISULFID
<222> LOCATION: (6)..(13)

<400> SEQUENCE: 12

Leu Arg Ala Val Gln Cys Arg Ser Val Glu Gly Ser Cys Gly Phe
1               5                   10                  15

<210> SEQ ID NO 13
<211> LENGTH: 15
<212> TYPE: PRT
<213> ORGANISM: Artificial
<220> FEATURE:
<223> OTHER INFORMATION: hGH 177 - 191 with Lysine at 179; cyclic
      peptide
<220> FEATURE:
<221> NAME/KEY: DISULFID
<222> LOCATION: (6)..(13)

<400> SEQUENCE: 13

Leu Arg Lys Val Gln Cys Arg Ser Val Glu Gly Ser Cys Gly Phe
1               5                   10                  15

<210> SEQ ID NO 14
<211> LENGTH: 15
<212> TYPE: PRT
<213> ORGANISM: Artificial
<220> FEATURE:
<223> OTHER INFORMATION: hGH 177 - 191 with Alanine at 180; cyclic
      peptide
<220> FEATURE:
<221> NAME/KEY: DISULFID
<222> LOCATION: (6)..(13)

<400> SEQUENCE: 14

Leu Arg Ile Ala Gln Cys Arg Ser Val Glu Gly Ser Cys Gly Phe
1               5                   10                  15

<210> SEQ ID NO 15
<211> LENGTH: 15
<212> TYPE: PRT
<213> ORGANISM: Artificial
<220> FEATURE:
<223> OTHER INFORMATION: hGH 177 - 191 with Alanine at 181; cyclic
      peptide
<220> FEATURE:
<221> NAME/KEY: DISULFID
<222> LOCATION: (6)..(13)

<400> SEQUENCE: 15

Leu Arg Ile Val Ala Cys Arg Ser Val Glu Gly Ser Cys Gly Phe
```

```
                1               5                  10                  15
```

<210> SEQ ID NO 16
<211> LENGTH: 15
<212> TYPE: PRT
<213> ORGANISM: Artificial
<220> FEATURE:
<223> OTHER INFORMATION: hGH 177 - 191 with Alanine at 184; cyclic
      peptide
<220> FEATURE:
<221> NAME/KEY: DISULFID
<222> LOCATION: (6)..(13)

<400> SEQUENCE: 16

```
Leu Arg Ile Val Gln Cys Arg Ala Val Glu Gly Ser Cys Gly Phe
1               5                  10                  15
```

<210> SEQ ID NO 17
<211> LENGTH: 15
<212> TYPE: PRT
<213> ORGANISM: Artificial
<220> FEATURE:
<223> OTHER INFORMATION: hGH 177 - 191 with Alanine at 185; cyclic
      peptide
<220> FEATURE:
<221> NAME/KEY: DISULFID
<222> LOCATION: (6)..(13)

<400> SEQUENCE: 17

```
Leu Arg Ile Val Gln Cys Arg Ser Ala Glu Gly Ser Cys Gly Phe
1               5                  10                  15
```

<210> SEQ ID NO 18
<211> LENGTH: 15
<212> TYPE: PRT
<213> ORGANISM: Artificial
<220> FEATURE:
<223> OTHER INFORMATION: hGH 177 - 191 with Alanine at 187; cyclic
      peptide
<220> FEATURE:
<221> NAME/KEY: DISULFID
<222> LOCATION: (6)..(13)

<400> SEQUENCE: 18

```
Leu Arg Ile Val Gln Cys Arg Ser Val Glu Ala Ser Cys Gly Phe
1               5                  10                  15
```

<210> SEQ ID NO 19
<211> LENGTH: 15
<212> TYPE: PRT
<213> ORGANISM: Artificial
<220> FEATURE:
<223> OTHER INFORMATION: hGH 177 - 191 with Alanine at 188; cyclic
      peptide
<220> FEATURE:
<221> NAME/KEY: DISULFID
<222> LOCATION: (6)..(13)

<400> SEQUENCE: 19

```
Leu Arg Ile Val Gln Cys Arg Ser Val Glu Gly Ala Cys Gly Phe
1               5                  10                  15
```

<210> SEQ ID NO 20
<211> LENGTH: 15
<212> TYPE: PRT
<213> ORGANISM: Artificial
<220> FEATURE:
<223> OTHER INFORMATION: hGH 177 - 191 with Alanine at 190; cyclic
      peptide
<220> FEATURE:
<221> NAME/KEY: DISULFID

```
<222> LOCATION: (6)..(13)

<400> SEQUENCE: 20

Leu Arg Ile Val Gln Cys Arg Ser Val Glu Gly Ser Cys Ala Phe
1               5                   10                  15

<210> SEQ ID NO 21
<211> LENGTH: 15
<212> TYPE: PRT
<213> ORGANISM: Artificial
<220> FEATURE:
<223> OTHER INFORMATION: hGH 177 - 191 with D-Alanine at 187 and 190;
      cyclic peptide
<220> FEATURE:
<221> NAME/KEY: DISULFID
<222> LOCATION: (6)..(13)
<220> FEATURE:
<221> NAME/KEY: Xaa
<222> LOCATION: (11)..(11)
<223> OTHER INFORMATION: D-Alanine
<220> FEATURE:
<221> NAME/KEY: Xaa
<222> LOCATION: (14)..(14)
<223> OTHER INFORMATION: D-Alanine

<400> SEQUENCE: 21

Leu Arg Ile Val Gln Cys Arg Ser Val Glu Xaa Ser Cys Xaa Phe
1               5                   10                  15

<210> SEQ ID NO 22
<211> LENGTH: 15
<212> TYPE: PRT
<213> ORGANISM: Artificial
<220> FEATURE:
<223> OTHER INFORMATION: hGH 177 - 191 with Alanine at 191; cyclic
      peptide
<220> FEATURE:
<221> NAME/KEY: DISULFID
<222> LOCATION: (6)..(13)

<400> SEQUENCE: 22

Leu Arg Ile Val Gln Cys Arg Ser Val Glu Gly Ser Cys Gly Ala
1               5                   10                  15
```